(12) United States Patent
Namiki et al.

(10) Patent No.: US 9,394,516 B2
(45) Date of Patent: Jul. 19, 2016

(54) SELF-RENEWAL PROMOTER FOR NEURAL STEM CELLS AND METHOD FOR USING SAME

(75) Inventors: Jun Namiki, Tokyo (JP); Hideyuki Okano, Tokyo (JP)

(73) Assignee: Keio University, Minato-ku, Tokyo (JP)

( * ) Notice: Subject to any disclaimer, the term of this patent is extended or adjusted under 35 U.S.C. 154(b) by 0 days.

(21) Appl. No.: 13/643,337

(22) PCT Filed: Apr. 26, 2011

(86) PCT No.: PCT/JP2011/060184
§ 371 (c)(1),
(2), (4) Date: Feb. 1, 2013

(87) PCT Pub. No.: WO2011/136233
PCT Pub. Date: Nov. 3, 2011

(65) Prior Publication Data
US 2013/0129708 A1    May 23, 2013

(30) Foreign Application Priority Data
Apr. 26, 2010  (JP) ................................ 2010-101415

(51) Int. Cl.
| | | |
|---|---|---|
| C12N 5/0797 | (2010.01) | |
| A61K 38/17 | (2006.01) | |
| C12N 5/06 | (2006.01) | |
| C12N 5/00 | (2006.01) | |
| C12N 5/07 | (2010.01) | |
| A61K 38/47 | (2006.01) | |
| C12N 9/42 | (2006.01) | |

(52) U.S. Cl.
CPC .......... *C12N 5/0623* (2013.01); *A61K 38/1709* (2013.01); *A61K 38/1735* (2013.01); *A61K 38/47* (2013.01); *C12N 5/0018* (2013.01); *C12N 5/06* (2013.01); *C12N 9/2442* (2013.01); *C12Y 302/01014* (2013.01); *C12N 2501/73* (2013.01)

(58) Field of Classification Search
CPC .... A61K 38/1709; C12N 5/06; C12N 5/0623; C12N 5/0018
See application file for complete search history.

(56) References Cited

U.S. PATENT DOCUMENTS

| | | | |
|---|---|---|---|
| 2004/0038888 A1* | 2/2004 | Mercer et al. ...................... | 514/12 |
| 2005/0163767 A1 | 7/2005 | Nakanishi et al. | |
| 2007/0259020 A1* | 11/2007 | Langer et al. .................. | 424/426 |

FOREIGN PATENT DOCUMENTS

WO     WO 01/36633 A1     5/2001

OTHER PUBLICATIONS

Kawada ("Chitinase 3-like-1 enhances baceterial adhesion to colonic epithelial cells through the interaction with bacterial chitin-binding protein" Laboratory Investigation (2008), 88, 883-895.*
Ceuninck Development of an enzyme linked immunoassay for the quantification of YKL-40 (cartilage gp-39) in guinea pig serum using hen egg yolk antibodies (Journal of Immunological Methods 252 (2001) 153-161.*
Hoover "Expression of the Chitinase Family Glycoprotein YKL-40 in Undifferentiated, Differentiated and Transdifferentiated Mesenchymal Stem Cells" PLOS One May 2013, vol. 8 Issue 5 1-8.*
Kawaguchi et al., "Nestin-EGFP transgenic mice: visualization of the self-renewal and multipotency of CNS stem cells," Mol Cell Neurosci. 17(2):259-73 (2001).
Okada et al., "Spatiotemporal recapitulation of central nervous system development by murine embryonic stem cell-derived neural stem/progenitor cells," Stem Cells. 26(12):3086-98 (2008).
Okano et al., "Transplantation of neural stem cells into the spinal cord after injury," Semin Cel Dev Biol. 14(3):191-8 (2003).
Ohtaki et al., "Stem/progenitor cells from bone marrow decrease neuronal death in global ischemia by modulation of inflammatory/immune responses," *Proceedings of the National Academy of Sciences of the United States of America* 105:14638-14643 (2008).
Owhashi et al., "Identification of a novel eosinophil chemotactic cytokine (ECF-L) as a chitinase family protein," *The Journal of Biological Chemistry* 275: 1279-1286 (2000).
Shen et al., "Endothelial cells stimulate self-renewal and expand neurogenesis of neural stem cells," *Science* 304: 1338-1340 (2004).
English Translation of International Search Report for PCT/JP2011/060184, mailed Jul. 19, 2011 (2 pages).
Namiki et al., "Shinkei Kansaibo no Jiko Fukusei ni kakawaru kekkan Naihi Zenku Saibo niche factor," Regenerative Medicine 7 (Suppl.):187 (2008) (English language translation provided).
Namiki et al., "A niche factor secreted from endothelial progenitor cells for self-renewal of neural stem cells," The 14th Congress of the Japanese Society for Regenerative Medicine, dated Mar. 13, 2008 (20 pages, English language translation provided).
Johansen et al., "Serum YKL-40, a new prognostic biomarker in cancer patients?," Cancer Epidemiol Biomarkers Prev 15(2):194-202 (2006).
Kzhyshkowska et al., "Human chitinases and chitinase-like proteins as indicators for inflammation and cancer," Biomarker Insights 2:128-146 (2007).

\* cited by examiner

*Primary Examiner* — Robert Yamasaki
*Assistant Examiner* — Charles Zoltan Constantine
(74) *Attorney, Agent, or Firm* — Clark & Elbing LLP

(57) ABSTRACT

An object of the present invention to provide an agent for promoting the self-renewal of the neural stem cells and a method of using the same. ECF-L contained in a culture supernatant of endothelial progenitor cells derived from bone marrow has an effect of promoting the self-renewal of neural stem cells. Accordingly, ECF-L can be used as an ingredient of an agent for promoting the self-renewal of the neural stem cells, a pharmaceutical composition for growing the neural stem cells, and a pharmaceutical composition for treating a disease associated with neural dysfunction.

2 Claims, 18 Drawing Sheets

*p<0.05

Flow chart of Examples 2, 5, and 7

* Conditioned medium of the primary cultured neurospheres n=20 *p<0.05 n=20  *p<0.05 n=3 *p<0.05 n=8 or 10  *p<0.001

Localization of ECF-L in the hippocampus

Localization of ECF-L in the lateral ventricle

Localization of ECF-L in the lateral ventricle

Localization of ECF-L in the cerebral cortex

SELF-RENEWAL PROMOTER FOR NEURAL STEM CELLS AND METHOD FOR USING SAME

CROSS REFERENCE TO RELATED APPLICATION

This application claims the benefit of Japanese Patent Application No. 2010-101415 filed on Apr. 26, 2010, the entire disclosure of which is hereby incorporated by reference.

TECHNICAL FIELD

The present invention relates to agents for promoting the self-renewal of neural stem cells and methods of using the same.

BACKGROUND ART

Neural stem cells are therapeutically effective donor cells for transplantation to treat severe neural dysfunctions caused by nerve injuries such as spinal cord injuries, and are thus promising for application in regenerative medicine (e.g., see, Okano H, Ogawa Y, Nakamura M, Kaneko S, Iwanami A, Toyama Y. (2003), Seminars in Cell & Developmental Biology 14(3): 191-198). For example, it has been considered to generate neural stem cells from undifferentiated cells such as embryonic stem cells (ES cells) or induced pluripotent stem cells (iPS cells) (e.g., see, Okada Y, Matsumoto A, Shimazaki T, Enoki R, Koizumi A, Ishii S, Itoyama Y, Sobue G, Okano H. (2008), Stem Cells 2008 Dec. 26(12): 3086-3098) and transplant these cells into a patient. Clinical applications of ES cells have, however, problems on ethical concerns or rejections in transplantation, while induced pluripotent stem cells (iPS cells) still have some unsolved issues associated with, for example, canceration and still have many problems to be solved for therapeutic applications.

On the other hand, if neural stem cells residing in the brain of a living body can be activated and increased, neural dysfunctions are expected to be improved without any transplantation of neural stem cells from other individual. It can be thought that at least problems of rejections and canceration will not arise.

At present, however, growth factors and regulatory factors of cell lineage are major candidates that have been investigated as factors possibly being involved in the promotion of self-renewal or activation of neural stem cells, which have not yet been definitely identified. This means that the proliferation of the neural stem cells cannot necessarily be controlled artificially. To increase the number of endogenous neural stem cells is thus hard to achieve.

Accordingly, an object of the present invention is to provide agents for promoting the self-renewal of neural stem cells and a method of using the same.

DISCLOSURE OF THE INVENTION

The present inventors have found that the self-renewal of the neural stem cells are promoted by ECF-L contained in a culture supernatant of endothelial progenitor cells derived from bone marrow, as described in the following Examples. The present invention has thus been completed.

More specifically, a promoting agent according to present invention is a promoting agent for promoting the self-renewal of a neural stem cell, comprising ECF-L or an expression vector capable of expressing ECF-L as an active ingredient.

It is preferable that the ECF-L contained in the promoting agent according to the present invention is human acidic chitinase, human chitotriosidase, human oviductal glycoprotein 1 precursor, human chitinase 3-like 2 or human chitinase 3-like 1.

A method of culturing a neural stem cell according to the present invention comprises culturing the neural stem cell in the presence of ECF-L.

It is preferable that, in the method of culturing neural stem cells according to the present invention, the ECF-L is human acidic chitinase, human chitotriosidase, human oviductal glycoprotein 1 precursor, human chitinase 3-like 2 or human chitinase 3-like 1.

A pharmaceutical composition according to the present invention is a pharmaceutical composition for promoting the self-renewal of a neural stem cell, comprising ECF-L or an expression vector capable of expressing ECF-L. It is preferable that this pharmaceutical composition is for treating a disease associated with neural dysfunction. The disease may be cerebral infarction, spinal cord injury, amyotrophic lateral sclerosis, Alzheimer's disease, Parkinson's disease, progressive supranuclear palsy, Huntington's disease, multiple system atrophy, spinocerebellar ataxia, intracerebral hemorrhage or subarachnoid hemorrhage. In addition, the neural dysfunction may be associated with normal aging.

It is preferable, in the pharmaceutical composition according to the present invention, that the ECF-L is human acidic chitinase, human chitotriosidase, human oviductal glycoprotein 1 precursor, human chitinase 3-like 2 or human chitinase 3-like 1.

A medicament according to the present invention comprises any one of the aforementioned pharmaceutical compositions.

MODE FOR CARRYING OUT THE INVENTION

Figure 1:
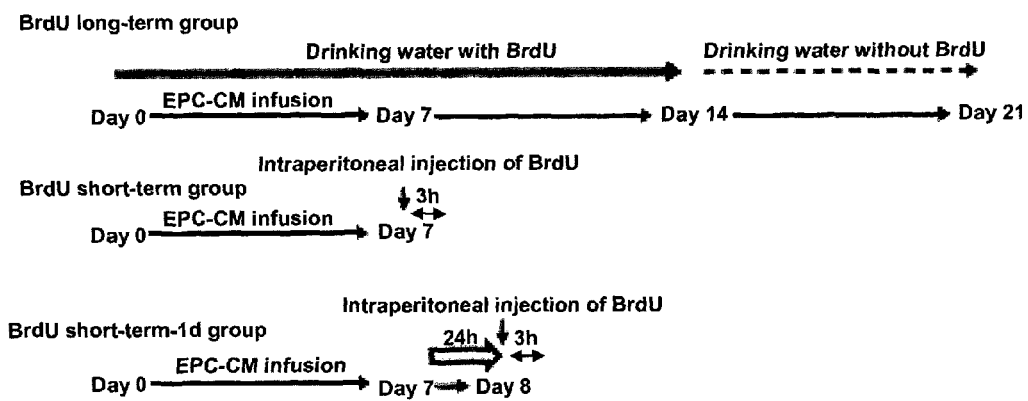
FIG. 1 is a figure showing operations in a BrdU long-term group, a BrdU short-term group, and a BrdU short-term-1d group when EPC-CM is infused into the brain of mice in one mode of Example.

An embodiment of the present invention that was completed based on the aforementioned finding is described below in detail in reference to Examples.

Unless otherwise noted in embodiments and examples, all procedures used are as described in standard protocols such as J. Sambrook, E. F. Fritsch & T. Maniatis (Ed.), Molecular cloning, a laboratory manual (3rd edition), Cold Spring Harbor Press, Cold Spring Harbor, N.Y. (2001); F. M. Ausubel, R. Brent, R. E. Kingston, D. D. Moore, J. G. Seidman, J. A. Smith, K. Struhl (Ed.), Current Protocols in Molecular Biology, John Wiley & Sons Ltd., with or without modifications or changes. In addition, unless otherwise noted, a commercial reagent kit or a measurement instrument, if any, is used as described according to protocols attached thereto.

The above and further objects, features, advantages, and ideas of the present invention are apparent from those skilled in the art from consideration of the detailed description of this specification. Furthermore, those skilled in the art can easily reproduce the present invention from these descriptions. The mode(s) and specific example(s) described below represent a preferable embodiment of the present invention, which is given for the purpose of illustration or description. The present invention is not limited thereto. It is obvious to those skilled in the art that various modifications may be made according to the descriptions of the present specification without departing from the spirit and scope of the present invention disclosed herein.

==ECF-L==

In this specification, ECF-L refers to a protein with an amino acid sequence of SEQ ID No. 1, homologs of a protein with the amino acid sequence of SEQ ID No. 1, or proteins with amino acid sequences encoded by orthologs of a gene encoding the amino acid sequence of SEQ ID No. 1. A homolog sharing higher homology with the amino acid sequence of SEQ ID No. 1 is preferable, such as, for example, homology of 60% or higher is preferable, homology of 70% or higher is more preferable, homology of 80% or higher is yet more preferable, homology of 90% or higher is still more preferable, and homology of 95% or higher is much more preferable. The amino acid sequence of ECF-L may be derived from any animal species and is not specifically limited as long as it can promote self-renewal of neural stem cells. However, it is preferable that the amino acid sequence of ECF-L is derived from the same species of the animal as that from which subject neural stem cells for the promotion of the self-renewal are derived. For example, it is preferable that ECF-L with an amino acid sequence derived from human is used when the self-renewal of neural stem cells derived from human is to be promoted. Examples of the ECF-L with an amino acid sequence derived from human, i.e., human homologs of ECF-L include acidic chitinase (isoform a (NCBI Accession No.: NP_068569.2) and isoform c (NCBI Accession No.: NP_970615.2)), chitotriosidase (NCBI Accession No.: NP_003456.1), oviductal glycoprotein 1 precursor (NCBI Accession No.: NP_002548.3), chitinase 3-like 2 (isoform a (NCBI Accession No.: NP_003391.2), isoform b (NCBI Accession No.: NP_001020368.1), and isoform c (NCBI Accession No.: NP_001020370.1)) chitinase 3-like 1 (NCBI Accession No.: NP_001267.2).

The ECF-L may have any mutation as long as its function of promoting the self-renewal of neural stem cells is not affected. For example, an amino acid sequence in which one or more amino acids are deleted, inserted or substituted is also included. In addition, post-translational modification such as glycosylation may be present as long as the function of promoting the self-renewal of neural stem cells is not affected.

==Agent for Promoting Self Renewal of Neural Stem Cells and Method of Producing the Same==

Culture of neural stem cells in the presence of ECF-L promotes the self-renewal of the neural stem cells. Therefore, a drug containing ECF-L as an active ingredient is useful as an agent for promoting the self-renewal of the neural stem cells.

ECF-L is not specifically limited by a method used to obtain or prepare it as long as it has a desired function of promoting their self-renewal. It may be a naturally occurring ECF-L or an artificial ECF-L. The naturally occurring ECF-L may be obtained from an animal tissue expressing ECF-L using, for example, an appropriate combination of well-known methods for isolating and purifying proteins. The artificial ECF-L may be produced using, for example, a well-known gene recombination technique or chemical synthesis. With the gene recombination technique, a process as an example may involve the introduction of a DNA with nucleotide sequence encoding ECF-L into an appropriate expression vector and the subsequent transfection of the expression vector into a host such as cultured cells to express a peptide. ECF-L may be isolated from a medium, or alternatively, medium may be used as it is. On the other hand, examples of the chemical synthesis include an Fmoc method (fluorenylmethyloxycarbonyl method) or a tBoc method (t-butyloxycarbonyl method). In addition, a variety of commercially available peptide synthesizers may be used to produce ECF-L.

Alternatively, the agent for promoting the self-renewal of the neural stem cells may contain an expression vector capable of expressing ECF-L. This expression vector has an appropriate promoter for expressing ECF-L in neural stem cells, and DNA encoding ECF-L downstream of the promoter. ECF-L is expressed by introduction of this expression vector into the cells. Thus, a medicament containing this expression vector can provide an effect of promoting the self-renewal similar to the medicament containing ECF-L, on the neural stem cells.

The promoting agent may contain one or more substances other than ECF-L, selected from substances that act on the neural stem cells and promote their self-renewal, substances effective for maintaining the neural stem cells, and substances that promote the proliferation of the neural stem cells. Examples of these substances include, but not limited to, EGF, FGF, VEGF, EDNF, PEDF, HGF, IGF, PDGF, and TGF.

This promoting agent may be formulated into a dosage form, if necessary, using a pharmaceutical additive such as a carrier, a diluent or an excipient that is other than the aforementioned active ingredient and is well-known to those skilled in the art. The dosage form is not specifically limited as long as it is suitable for a promoting agent. The promoting agent may be formulated into a tablet, a capsule, an emulsion, a liquid, granules, particles, powders, and paste.

==Method for Culturing Neural Stem Cells==

Neural stem cells are self-renewing, multipotent cells that can differentiate into neuronal and glial cells. Culture of neural stem cells in the presence of ECF-L can suppress their asymmetric division and successive differentiation into glial progenitors, effectively causing the self-renewal of only the neural stem cells.

The neural stem cells to be allowed to proliferate are not limited by a method used to obtain them. For example, a tissue from which the neural stem cells are isolated is not limited as long as it contains the neural stem cells. Preferable examples include a central nervous tissue of an animal, in particular, hippocampus, lateral ventricle or its periphery. The stage of the development or growth of the animal is not specifically limited as long as desired neural stem cells are obtained, including a fetus, a premature individual, and an adult. While the species of the animal from which the neural stem cells are derived is not specifically limited, it is preferable that the animal is a human or a mammal other than the human.

When neural stem cells are prepared from a tissue, a tissue sample may be pretreated appropriately. For example, when neural stem cells are involved in cell aggregates, the involved cells may be dissociated physically by pipetting or chemically with an enzyme. The enzyme may be selected from those used routinely such as trypsin and collagenase.

Alternatively, neural stem cells may be differentiated from embryonic stem cells (ES cells) or induced pluripotent stem cells (iPS cells). For example, ES cells or iPS cells are cultured in the presence of a low concentration of retinoic acid ($10^{-9}$M to $10^{-6}$M) to form embryoid bodies (EBs). EBs may be formed by adding Noggin protein to a medium of pluripotent stem cells derived from differentiated cells. Specifically, the noggin gene of *Xenopus laevis* is introduced into cultured mammalian cells to transiently express the Noggin protein. The resulting culture supernatant may be used (1 to 50% (v/v)) as it is. Alternatively, recombinant noggin protein (ca. 1 μg/ml) may be used. By dissociating the EBs thus obtained, the neural stem cells can be differentiated into neurospheres and then culturing them in a serum-free medium supplemented with bFGF (10 to 100 ng/ml).

The neural stem cells thus obtained are centrifuged (500 to 2000 rpm, 3 to 10 minutes) and the precipitated cells are resuspended in a medium to prepare a cell suspension. Then, the cells are seeded in plates at 10000 to 20000 cells/cm$^2$, and incubated at 37° C. under 5% $CO_2$.

The medium used is not specifically limited as long as the neural stem cells can be cultured. Examples include α-MEM (α-minimum essential medium), DMEM (Dulbecco's modified Eagle's medium), and IMDM (Isocove's modified Dulbecco's medium). An agent for promoting the self-renewal of the neural stem cells containing an effective amount of ECF-L is added to the medium to promote their self-renewal. The effective concentration of the ECF-L is not specifically limited, and those skilled in the art can appropriately determine it depending on the neural stem cells to be cultured.

The medium may contain, other than ECF-L or the agent for promoting the self-renewal of the neural stem cells, an antibiotic such as penicillin and streptomycin and a growth factor (e.g., EGF, bFGF, TGF-α, and LIF) effective for maintaining the neural stem cells or promoting their proliferation, which are typically used for culturing cells.

==Use of Self-Renewed Neural Stem Cells==

The neural stem cells that have been self-renewed using a culture method according to the present invention are highly useful in the field of regenerative medicine. For example, transplantation of a necessary amount of self-renewed neural stem cells into a dysfunctional neural tissue brings about differentiation of newborn neurons at the site of transplantation, regenerating the tissue. In such a case, it is preferable that the species of the animal (donor) from which the neural stem cells to be transplanted are obtained is identical to the species of the animal (recipient) that will undergo transplantation. It is more preferable that the donor is the same as the recipient, but it is not necessarily so. In addition, a method of preparing the self-renewed neural stem cells for use in transplantation is not specifically limited and those skilled in the art can determine an appropriate method. For example, the self-renewed neural stem cells may be suspended in medium or buffer. Alternatively, they may be prepared as cell aggregates or cell sheets. The disease of the aforementioned recipient is not specifically limited as long as the condition of the recipient is expected to be improved after transplantation of the neural stem cells. Diseases associated with neural dysfunction are preferable, and examples include traumatic injuries such as spinal cord injury, neurodegenerative diseases such as amyotrophic lateral sclerosis, Alzheimer's disease, Parkinson's disease, progressive supranuclear palsy, Huntington's disease, multiple system atrophy, and spinocerebellar ataxia, and neuronal death due to, for example, intracerebral hemorrhage, subarachnoid hemorrhage, and cerebral infarction. In addition, neural dysfunction associated with normal aging, if any, can also be treated by transplanting self-renewed neural stem cells.

==Pharmaceutical Composition Containing ECF-L==

A pharmaceutical composition for growing the neural stem cells according to the present invention comprises ECF-L or an expression vector capable of expressing ECF-L.

Culture of neural stem cells in the presence of ECF-L promotes the self-renewal of the neural stem cells. Accordingly, when a pharmaceutical composition containing ECF-L as an active ingredient is administered to a patient with a disease associated with neural dysfunction, the self-renewal of the neural stem cells of the patient himself or herself is promoted and the neural stem cells are allowed to proliferate. These neural stem cells generate new neurons, thus leading to regeneration of the tissue.

Examples of diseases associated with neural dysfunction include traumatic injuries such as spinal cord injury, neurodegenerative diseases such as amyotrophic lateral sclerosis, Alzheimer's disease, Parkinson's disease, progressive supranuclear palsy, Huntington's disease, multiple system atrophy, and spinocerebellar ataxia, and neuronal death due to, for example, intracerebral hemorrhage, subarachnoid hemorrhage, and cerebral infarction. The dysfunction of the neural stem cells may be associated with normal aging.

The pharmaceutical composition according to the present invention contains ECF-L as an active ingredient. The concentration of ECF-L in the pharmaceutical composition can be appropriately determined by those skilled in the art in consideration of the final concentration required for allowing the neural stem cells to proliferate. This pharmaceutical composition may contain one or more substances other than ECF-L, selected from substances that act on the neural stem cells and promote their self-renewal, substances effective for maintaining them, and substances that promote their proliferation. Examples of these substances include, but not limited to, EGF, FGF, VEGF, PEDF, HGF, IGF, PDGF, and TGF.

A medicament produced by formulating a pharmaceutical composition containing ECF-L as an active ingredient can be used for treating diseases associated with neuronal dysfunction.

This medicament is formulated into a dosage form with, if necessary, a pharmaceutically acceptable carrier. The pharmaceutically acceptable carrier used herein can be appropriately from ordinary carriers depending on the pharmaceutical composition to be prepared. The form of the medicament is not specifically limited as long as the form is suitable for treatment. The medicament may be formulated as oral drugs such as a tablet, a capsule, granules, powders, syrup, a enteric-coated tablet, a controlled-release capsule, a cachou, a chewable tablet, a drop, a pill, oral liquid, a confectionery tablet, a controlled-release tablet, and controlled-release granules. The medicament may be formulated as injectables such as liquid injections, emulsion injections, and solid injections. This medicament may be combined with a different pharmaceutical composition along with the aforementioned pharmaceutical additives.

It is not limited whether the present medicament contains one of the aforementioned pharmaceutical composition according to the present invention as an active ingredient or it contains two or more of them. This can be appropriately determined by those skilled in the art. It is preferable that ECF-L in the pharmaceutical composition contained in this medicament is derived from the same species of the animal as the subject to which the medicament is to be administered. For example, when the medicament is administered to a human, it is preferable that a pharmaceutical composition containing ECF-L derived from human.

As to how to administer the medicament according to the present invention, a necessary amount of the medicament can be administered using a suitable method to a subject animal within a range of dose that is considered to be safe. The dose of the medicament for therapy according to the present invention is appropriately determined by a physician or a veterinarian in consideration of, for example, the type of the dosage form, the method of administration, the age and weight of the subject, and the condition of the subject.

The animal to which the medicament according to the present invention is administered is not specifically limited as long as the animal is suffering from a disease that can be alleviated by the proliferation of the neural stem cells as described above. It is, however, preferable that the animal is a human or a mammal other than human. It is more preferable that the animal is a human.

EXAMPLES

Experimental Method

==Method of Counting Living Cells==

10 µl of trypan blue and 10 µl of a suspension of endothelial progenitor cells derived from bone marrow was mixed and the mixture was dropped on a hemocytometer. The number of unstained cells in 16 squares (each square is 250 by 250 µm) was counted. Since trypan blue stains dead cells, unstained cells are living cells.

==Fixation of Mouse Tissue==

Mice were anesthetized with diethyl ether, and PBS was gently perfused into the left ventricle of each mouse with a 23-gauge needle connected to a perfusion pump which is filled with 50 ml of PBS. After the liver turns from red to gray, 50 to 75 ml of 4% paraformaldehyde (pH 7.4) was perfused in place of PBS to fix the tissue.

==Method of Making Frozen Sections==

The brain tissue fixed in the manner described above was removed, post-fixed overnight in 4% paraformaldehyde at 4° C., and then incubated overnight in 30% glucose-PBS solution. Thymic tissue was similarly treated as a positive control for the proliferated cells.

Forebrain was isolated from the aforementioned brain tissue and embedded in O.C.T. compound (Tissue Tek, Sakura Finetec U.S.A.). Eighty five coronal sections each having a thickness of 14 μm were made from 1.2 mm frozen tissue between the rostral forebrain to the third ventricle. These sections were mounted on MAS coated glass slides (Matsunami Glass Ind., Ltd.).

==Immunohistochemical Staining==

The sections were washed with PBS for 10 minutes. 150 μl of 0.3% Triton X-100-PBS was added dropwise onto the sections, which were incubated for 3 minutes. The sections were then incubated at 4° C. overnight or at 37° C. for 3 hours with a primary antibody diluted with a blocking buffer. As a control for immunostaining, the control sections were incubated only with the blocking buffer. The sections were washed with PBS for 10 minutes three times, and incubated at room temperature for 1 hour with a secondary antibody. The sections were washed with PBS for 10 minutes three times, and incubated for 10 minutes with Hoechest 33258 (Sigma-Aldrich) diluted 1:1000 in PBS to counterstain the nuclei. The sections were washed twice with PBS for 10 minutes and then washed with sterile distilled water for 5 minutes. The sections were mounted with a mounting medium and observed under a fluorescence microscope or a confocal laser scan microscope.

Example 1

This Example shows that a culture supernatant of endothelial progenitor cells (endotherial progenitor cell-conditioned medium, EPC-CM) derived from mouse bone marrow has an effect of promoting the self-renewal of neural stem cells and an effect of increasing the number of their progeny in vivo.

==Isolation of Cells Derived from Bone Marrow==

Adult mice (C57BL/6J, male, 8 to 10 weeks of age, n=10) were anesthetized with diethyl ether and sacrificed by decapitation or cervical spine dislocation. After they were wiped with alcohol, femur and tibia were removed and kept in PBS/6-cm dish on ice. Muscle tissues and tendons were cleared away from these bones using Kimwipes (Nippon Paper Crecia Co., Ltd.) soaked with 70% ethanol. The bones of ten mice were put into a mortar filled with 6 ml of αMEM/FBS (αMEM supplemented with 10% FBS, 100 units/ml penicillin, and 100 μg/ml streptomycin) and were ground. This bone powder suspension was filtered by centrifugation through a filter of 70 μm (cell strainer 2350, Falcon), and the filtered cell suspension was recovered. The cell suspension was centrifuged at 280×g for 8 minutes, and the cell pellet thus obtained was resuspended by pipetting in 5 ml of αMEM/FBS.

==Isolation of Mononuclear Cells by Ficoll==

5 ml of cell suspension was overlaid on 5 ml of cold Ficoll (Ficoll-Paqie Plus (1077 g/ml), GE Healthcare Biosciences, Inc.). This was centrifuged at 780×g for 15 minutes at 4° C. The top layer was aspirated, leaving 2 ml of the layer. A pipette filled with 8 ml of αMEM/FBS was inserted into the bottom of the remaining top layer to collect the intermediate layer (layer of the mononuclear cells) of about 2 ml. This intermediate layer was centrifuged at 280×g for 8 minutes and the top layer was then discarded. The cell pellet was resuspended by pipetting in 2 ml of EGM-2 BulletKit medium (Lonza), which was used as bone marrow mononuclear cell suspension.

The number of cells was counted by the method of counting living cells described above.

==Culture of Endothelial Progenitor Cells Derived from Bone Marrow==

First, fibronectin solution (50 μl of 1 mg/ml fibronectin stock diluted with 25 ml of PBS) was added to each well of 6-well plates, in a volume of 3 ml per well. They were incubated overnight at 37° C. and washed with PBS to provide fibronectin-coated plates.

Next, the bone marrow mononuclear cells obtained by using the aforementioned isolation by Ficoll were seeded in 6-well, fibronectin-coated plates at $1 \times 10^6$ cells/ml with EGM-2 BulletKit medium, and incubated at 37° C., 5% $CO_2$. On 24 hours, 7 days, and 14 days after seeding, the medium was replaced with 3 ml of fresh EGM-2 BulletKit medium, and the culture was continued until adherent cells became confluent. With this method that is suitable for proliferation of the endothelial cells, only the endothelial progenitor cells selectively proliferated from the bone marrow mononuclear cells after 21 days of culture. These cells were fixed with 4% paraformaldehyde, and identified as endothelial progenitor cells by confirming positive reactions for CD31 and VE-cadherin immunostaining as well as their acetylated-LDL uptake ability, which was examined by adding acetylated-LDL labeled with DiI to the culture medium before the fixation of the cells and determining DiI-LDL uptake based on DiI fluorescence in the cells.

==Collection of Culture Supernatant of Endothelial Progenitor Cells Derived from Bone Marrow==

On the 21st day after seeding, a culture medium of the endothelial progenitor cells derived from bone marrow was aspirated, and the cells were washed with 1 ml of MHM medium (DMEM-F12 (1:1), glucose (0.6%), glutamine (2 mM), sodium biocarbonate (13.4 mM), HEPES (5 mM), insulin (25 μg/ml), transferrin (100 μg/ml), progesterone (20 nM), sodium selenate (30 nM), and purescine (60 μM), Murayama et al., Journal of Neuroscience Research, 69: 837-847, 2002). Then, 1 ml of MHM was added and the culture was continued for additional 24 hours. Thereafter, the medium was collected and filtered through a 0.45 μm filter to produce a conditioned medium of endothelial progenitor cells (EPC-CM). The conditioned medium was stored at −20° C. until use, if necessary.

==Preparation of Conditioned Medium of Endothelial Progenitor Cells Derived from Bone Marrow==

The aforementioned collected EPC-CM was filtered by centrifugation at 2380×g for 30 minutes using Amicon Ultra 15 centrifuge filter devices (10K NMWL, UFC9010, Millipore) and the conditioned medium left on the filter was collected with a pipette. As a result, the EPC-CM was concentrated about 45 times. This was used as concentrated EPC-CM and was stored at −20° C. until use, if necessary.

==Attachment of Infusion Assembly to Brain of Mice==

The concentrated EPC-CM was infused into the cerebral ventricles of mice using Alzet Brain Infusion Kit 3 (0008851, Alzet) and an Alzet osmotic pump (1007D, Alzet). First, the catheter tubing of this infusion assembly was cut to 2 cm. One end of the catheter tubing was attached to a cannula for brain infusion and the other end was attached to the Alzet pump flow moderator. The connections were glued to each other using cyanoacrylate adhesive. In addition, a depth adjustment spacer of 0.5 mm thick was attached to the cannula for brain infusion and glued using cyanoacrylate adhesive. This adjusted the depth of the remaining cannula tube from 3 mm to 2.5 mm. The Alzet osmotic pump was filled with the concentrated EPC-CM or αMEM (vehicle, control). A tip of a needle was attached to the free end of the Alzet pump flow moderator through an appropriate length of remaining catheter tubing, and the concentrated EPC-CM or concentrated αMEM (control) concentrated in a similar manner was delivered from a syringe to the infusion assembly. Thereafter, the syringe and the catheter tubing connected to the syringe were detached and the Alzet osmotic pump was connected to the free end of the Alzet flow moderator.

Mice (C57BL/6J, male, 8 weeks of age) were anesthetized by inhalation (induced with 4% isoflurane and maintained in 0.35 l/min. $N_2O$, 0.15 l/min. $O_2$) and fitted into a stereotaxic apparatus on a heat insulation pad. Incision was made starting slightly behind the eyes to expose the skull. Then, periosteal connective tissue which adheres to the skull was removed using a spatula.

A subcutaneous pocket was made in the midscapular area of the back of each mouse and the osmotic pump was inserted into the pocket. The osmotic pump was connected to the catheter tubing which, in turn, is connected to the cannula for brain infusion.

Anatomical points on the skull, i.e., bregma and lambda were determined. With these points as reference, location for placing cannula for brain infusion was determined (0 mm anteroposterior, −1.2 mm lateral, −2.3 mm dorsoventral to bregma). At this position, a hole of about 1 mm was formed through the skull using an electric drill.

The skull was dried, and several drops of cyanoacrylate adhesive were applied to around the hole. The cannula for brain infusion was inserted using the hole. After the cannula was properly glued in place with adhesive, a tab used for holding the cannula was cut away and then the scalp was sutured.

Mice removed from the stereotaxic apparatus were recovered from anesthesia and returned to a cage. The mice were fed for 7 days while infusing the concentrated EPC-CM or the concentrated αMEM medium at a rate of 0.5 μl per hour using the Alzet osmotic pump.

==Labeling of Dividing Cells with BrdU and Detection of BrdU-Labeled Dividing Cells==

To these mice, BrdU was administered as described below to detect neural stem cells and their progeny.

It is known that progeny of neural stem cells capable of dividing proliferate rapidly, while the neural stem cells proliferate slowly. BrdU can label the cells undergoing DNA synthesis in the course of administration because it is incorporated into newly synthesized DNAs when administered. In the BrdU-labeled cells, the incorporated BrdU is diluted as the cells divide repeatedly. Accordingly, in the progeny that proliferate rapidly, BrdU is more rapidly diluted in the labeled cells after the administration of BrdU. In the neural stem cells that proliferate slowly, the BrdU label can be remained for a longer period of time.

Taking advantage of this fact, ErdU was administered in different schedules for a BrdU short-term group, a BrdU short-term-1d group, and a BrdU long-term group as shown in FIG. 1 to independently detect the neural stem cells and their progeny (see, F. Doetsch, I. Caille, D. A. Lim, J. M. Garcia-Verdugo, A. Alvarez-Buylla (1999), Subventricular zone astrocytes are neural stem cells in the adult mammalian brain. Cell 97, 703-716; C. M. Morshead, C. G. Craig, D. van der Kooy (1998), In vivo clonal analyses reveal the properties of endogenous neural stem cell growth in the adult mammalian forebrain. Development 125, 2251-2261). More specifically, BrdU was administered once, and only the rapidly proliferating progeny was labeled and detected in the BrdU short-term group and the BrdU short-term-1d group. On the other hand, in the BrdU long-term group, BrdU was administered for a long time and both of the neural stem cells and their progeny whose DNA was synthesized were labeled. BrdU was, however, diluted in the labeled progeny in a subsequent period during which no BrdU was administered. Accordingly, only the labeled neural stem cells were detected (see, for example, Kawaguchi et al., Molecular Cell Neuroscience, 17: 259-273, 2001). A specific example of an experimental method is given below.

First, a BrdU stock solution was prepared by dissolving 25 mg of BrdU (B5002, Sigma-Aldrich) per 1 ml of 0.9% NaCl containing 0.007 N of NaOH.

Mice were given drinking water prepared by adding 8 ml of BrdU stock solution to 200 ml of water for total 14 days after the placement of the infusion assembly into the brain. Then, the mice were given regular drinking water without BrdU for one week (FIG. 1, n=7 for all of the BrdU long-term group, the concentrated EPC-CM administration and the concentrated αMEM administration).

Alternatively, 7 days after the placement of the infusion assembly, the aforementioned BrdU stock solution was injected intraperitoneally in such a manner that 50 μg of the stock solution is administered per 1 g of body weight and the mice were kept for additional 3 hours (FIG. 1, n=3 for all of the BrdU short-term group, the concentrated EPC-CM administration and the concentrated αMEM administration).

Alternatively, 7 days after the placement of the infusion assembly, mice were anesthetized by inhalation (included with 4% isoflurane and maintained in 0.35 l/min. $N_2O$, 0.15 l/min. $O_2$, and 1.5% isoflurane) to open the site sutured when the infusion assembly had been placed. The tube of the infusion assembly was cut and the open end connected to the cannula for infusion was closed using cyanoacrylate adhesive. Thereafter, the opened site was again sutured. On the following day, the aforementioned BrdU stock was injected intraperitoneally in such a manner that 50 μg of the stock is administered per 1 g of body weight and the mice were kept for additional 3 hours (FIG. 1, n=4 for the BrdU short-term-1d group and concentrated EPC-CM administration, n=5 for concentrated αMEM administration).

Only the cells whose DNA was synthesized at the time of BrdU administration, i.e., the rapidly proliferating progeny were labeled in the BrdU short-term group and the BrdU short-term-1d group in which the mice were sacrificed 3 hours after the administration of BrdU. In the BrdU long-term group, both of the neural stem cells and their progeny whose DNA was synthesized during the BrdU administration period for 14 days were labeled. In the rapidly proliferating progeny of the labeled cells, BrdU was distributed as the progeny divide in one week after the completion of the BrdU administration and BrdU is diluted. On the other hand, in the slowly proliferating neural stem cells of the labeled cells, BrdU label remained even after the lapse of one week from the completion of the BrdU administration.

Tissues of the mice that have been given BrdU as described above were fixed using a method of fixing mouse tissue, and the BrdU-labeled dividing cells were detected in a manner described below.

First, the cannula was pulled off from the skull and a brain tissue was removed from the skull to make frozen tissue sections. These sections were incubated in 1 N HCl at 37° C. for 30 minutes and labeled using immunohistochemical staining. For this purpose, PBS supplemented with 10% normal donkey serum was used as a blocking buffer, and anti-BrdU sheep antibody (20-BS17, Fitzgerald, 1:500 dilution) and Alexa Fluor 568 donkey anti-sheep IgG antibody (A-21099, Molecular Probes, 1:1000 dilution) were used as primary antibody and secondary antibody, respectively, to detect BrdU. As mounting medium, PermaFluor Mounting Medium (Lab Vision Corp.) was used.

From the 85 frozen coronal sections prepared, 8 sections were selected per 10 sections. The number of the BrdU-labeled cells on the side into which the concentrated EPC-CM or αMEM was infused was counted by a fluorescence microscope, using the nuclei of cells stained with Hoechest 33258 as marker, for the subventricular zone of the lateral ventricle where cells are gathered around the lateral ventricle, which is a target area of cell counting. A statistical analysis with t-study was performed on the number of the BrdU-labeled cells for the administration of the concentrated EPC-CM and the αMEM in each group.

Figure 2:
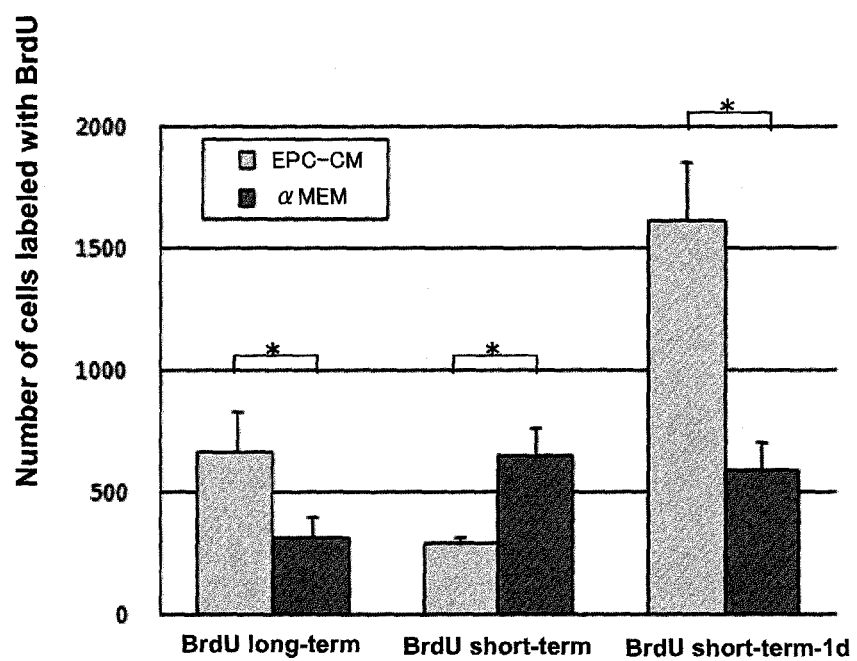
FIG. 2 is a graph showing the number of cells labeled with BrdU when EPC-CM is infused into the brain of mice in one embodiment of the present invention.

As shown in FIG. 2, in the BrdU long-term group, the BrdU-labeled cells around the lateral ventricle was significantly more in the group in which the concentrated EPC-CM was infused than in the group in which the concentrated αMEM was infused. This indicates that the neural stem cells were increased in the group in which the concentrated EPC-CM was infused. On the other hand, in the BrdU short-term group, the BrdU-labeled cells was significantly less in the group in which the concentrated EPC-CM was infused than in the group in which the concentrated αMEM was infused. This indicates that less progeny were present in the group in which the concentrated EPC-CM was infused. In the BrdU short-term-1d group, the BrdU-labeled cells was significantly more in the group in which the concentrated EPC-CM was infused than in the group in which the concentrated αMEM was infused. This indicates that more progeny were present in the group after the lapse of one day from the infusion of the concentrated EPC-CM.

The aforementioned results indicate that the infusion of the concentrated EPC-CM promotes the self-renewal of the neural stem cells around the lateral ventricle and suppresses the asymmetric division that produces progeny. In addition, the results also indicate that one day after the completion of the infusion of the concentrated EPC-CM, the neural stem cells increased by the self-renewal divide and the number of progeny is increased accordingly.

As apparent from the above, EPC-CM contains a substance having an effect of promoting the self-renewal of the neural stem cells. As result of increase of the number of the neural stem cells by their self-renewal, the number of progeny of the neural stem cells also increases.

Example 2

This Example shows that EPC-CM collected in Example 1 promotes the self-renewal of neural stem cells in vitro.
==Preparation of Marrow Stromal Cell-Conditioned Medium==

As a control for the conditioned medium of endothelial progenitor cells (EPC-CM) derived from bone marrow, a conditioned medium of marrow stromal cells (MSC-CM) was prepared, which are derived from bone marrow and secrete growth factors like the endothelial progenitor cells derived from bone marrow. First, marrow stromal cells were cultured as follows. Cell pellet obtained by centrifuging a bone powder suspension from adult mice (C57BL/6J, male, 8 to 10 weeks of age, n=2) were resuspended in αMEM/FBS, in a manner similar to that described in Example 1.

The number of living cells in 16 squares was counted by the method of counting living cells as described above. In this counting, 40 µl of cell suspension was mixed with 10 µl of trypan blue.

Next, the cells were seeded in 6-well, fibronectin-coated plates at a cell density of $5 \times 10^6$ cells per 1 ml of suspension with αMEM/FBS medium, and incubated at 37° C., 5% $CO_2$. On 24 hours, 7 days, and 14 days after seeding, the medium was replaced with 3 ml of fresh αMEM/FBS medium, and the culture was continued until cells became confluent.

After the primary cultured cells have become confluent, they were washed with PBS and treated with 1 ml of trypsin/EDTA (0.25%) at 37° C. for about 15 minutes. Thereafter, the cells were washed with 10 ml of αMEM/FBS to stop the enzymatic reaction. The cells were scraped with a cell scraper (541070, Greiner), and transferred to a 50 ml centrifuge tube with a pipette. The cells were centrifuged at 280×g for 8 minutes, after which the supernatant was discarded and the cell pellet was resuspended in 2 ml of αMEM/FBS. The number of living cells in the cell suspension thus obtained was counted by the method of counting living cells as described above. The cells were seeded on new culture dishes at a cell density of about 8000 cells/cm² to subculture them.

After the subcultured cells have become confluent, the culture supernatant of marrow stromal cells (marrow stromal cell-conditioned medium, MSC-CM) was collected in a manner similar to that described in Example 1.
==Assay of Neurospheres Derived from Fetal Mice==

With in vitro culture in suspension of cells isolated from a striatum of one hemisphere, floating neurospheres composed of neural stem cells and neural progenitor cells can be produced. It is shown below that a substance that promotes the self-renewal of the neural stem cells is contained in EPC-CM on the basis of the fact that a frequency of neurosphere formation is increased after the subculture of the cells with EPC-CM.

First, the uterus was removed from a pregnant adult mouse (ICR E14, female) and placed in a 10-cm dish containing ice-cold PBSG (PBS supplemented with 0.6% (v/v) glucose). In a clean bench, heads of eight fetuses removed from the uterus were isolated and placed in a 10-cm dish containing ice-cold PBSG.

Skin and the skull were incised symmetrically between the skull and the eyes in the head under a stereomicroscope. Furthermore, the brain tissue was opened to expose a lateral ventricle. A gray striatum found in a lumen of the lateral ventricle was isolated with ophthalmologic scissors and forceps and placed in a new 10-cm dish containing ice-cold PBSG.

The brain tissue thus isolated was transferred to a centrifuge tube containing 800 µl of MHM and dissociated by pipetting. The number of cells was counted by the method of counting living cells as described above.

The cells thus obtained were seeded at a density of $2 \times 10^5$ cells/ml in flasks of 75 cm² containing MHM supplemented with 20 ng/ml of bFGF (Peprotech) and 20 ng/ml of EGF (both final concentration), and incubated at 37° C., 5% $CO_2$.

On or around the third day after seeding, formation of neurospheres was recognized. On the seventh day after seeding, most of the neurospheres were 100 µm or larger.

Figure 3:
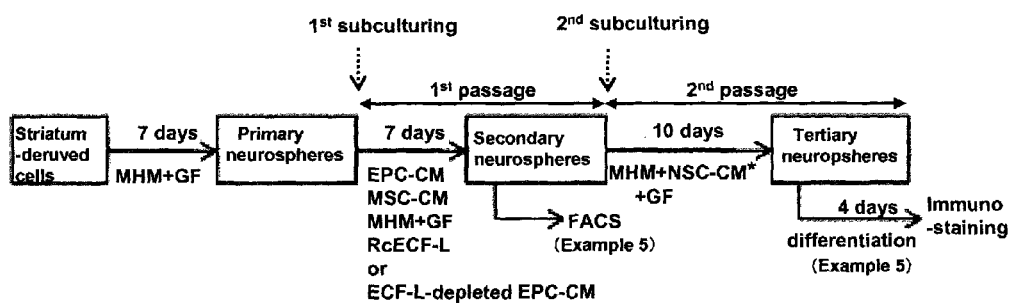
FIG. 3 is a flow chart of a neurosphere assay (Examples 2, 5, and 7) performed in one embodiment of the present invention.

With the neurospheres (primary neurospheres) thus obtained, effects of EPC-CM and MSC-CM on the self-renewal of the neural stem cells were examined. A specific procedure of a neurosphere assay is shown in FIG. 3.

In this assay, neurospheres were cultured under various conditions at the first passage after subculturing of the primary neurospheres, and cultured under an optimum condition at the second passage.
(First Passage)

The primary neurospheres in the flask were transferred to a centrifuge tube and centrifuged at 400 rpm for 5 minutes. The supernatant was discarded and 2 ml of MHM was added to the cell pellet to resuspend the neurospheres. The neurospheres were disrupted by pipetting to prepare cell suspension. This suspension was left stand for several minutes to precipitate the remaining neurospheres. The supernatant (1.5 ml) containing only the dispersed cells was transferred to a new centrifuge tube. In addition, 1.5 ml of MHM was added to the bottom layer containing the neurospheres, and the neurospheres were disrupted again by pipetting and left stand for 2 minutes. 1.5 ml of supernatant was mixed with the first supernatant collected previously. Then, 2 ml of MHM was added thereto and the suspension was centrifuged at 800 rpm for 5 minutes. The supernatant was aspirated and 1 ml of MHM was added to the cell pellet to resuspend the cells.

At this stage, the number of cells was counted by the method of counting living cells as described. The cell suspension was adjusted with EPC-CM or MSC-CM to a density of $15 \times 10^4$ cells/3 ml and seeded in a 6-well plate (3471 Ultra Low Cluster, Coster). For the analysis of the frequency of neurosphere formation, the cells were adjusted to a density of 2,000 cells/200 µl and seeded in a 96-well plate (3474 Ultra Low Cluster, Coster), 36 wells for each of EPC-CM and MSC-CM. To the wells containing a growth factor (18 wells for each of EPC-CM and MSC-CM), 20 ng/ml of bFGF and 20 ng/ml of EGF (both final concentration) were added and the cells were cultured at 37° C., 5%. $CO_2$.

Formation of secondary neurospheres was recognized on or around the third day after seeding.
(Second Passage)

The secondary neurospheres seeded in the 6-well plate was transferred as in the case of the first subculturing. The cell pellet obtained after the number of cells was counted was resuspended in a 1:1 mixture of MUM supplemented with 20 ng/ml of bFGF and 20 ng/ml of EGF (both final concentration) and the culture supernatant of the primary culture of the neurospheres to adjust to a density of 2,000 cells/200 µl. These cells were seeded in a 96-well plate and cultured at 37° C., 5% $CO_2$ for 10 days.
(Analysis of Frequency of Neurosphere Formation)

The number of neurospheres with a diameter of larger than 50 µm in each well, which are obtained in culture at the aforementioned first or second passage, was counted. A percentage of the number of the tertiary neurospheres with respect to the number of seeded cells was considered as a frequency of neurosphere formation.

Neurospheres are composed of self-renewed neural stem cells and neural progenitor cells derived from a single neural stem cell. Under optimum conditions for the culture of neurospheres, each of the neural stem cells included in the seeded cells gives rise to neurospheres. The culture condition at the second passage in this Example is the optimum conditions of the culture of the neurospheres. Thus, the frequency of neurosphere formation represents a ratio of the neural stem cells included in the secondary neurospheres obtained under the culture condition at the first passage. This means that the frequency of tertiary neurosphere formation at the second passage is increased when the self-renewal of the neural stem cells is promoted under the culture condition at the first passage.

Figure 4:
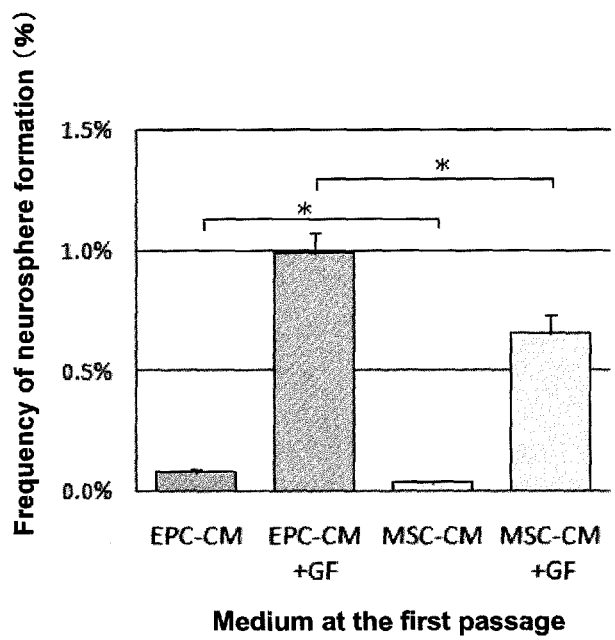
FIG. 4 is a graph showing a frequency of neurosphere formation when EPC-CM, GF-containing EPC-CM, MSC-CM or GF-containing MSC-CM was used as medium at the first passage of neural stem cells in one embodiment of the present invention.

As shown in FIG. 4, the frequency of neurosphere formation was significantly high at the first passage in a group (EPC-CM+GF group) in which the cells were cultured at the first passage with EPC-CM supplemented with a growth factor and a group (EPC-CM group) in which the cells were cultured with EPC-CM, compared to a group (MSC-CM+GF group) in which the cells were cultured with MSC-CM supplemented with a growth factor (GF) and a group (MSC-CM group) in which the cells were cultured with MSC-CM (t-study).

Figure 5:
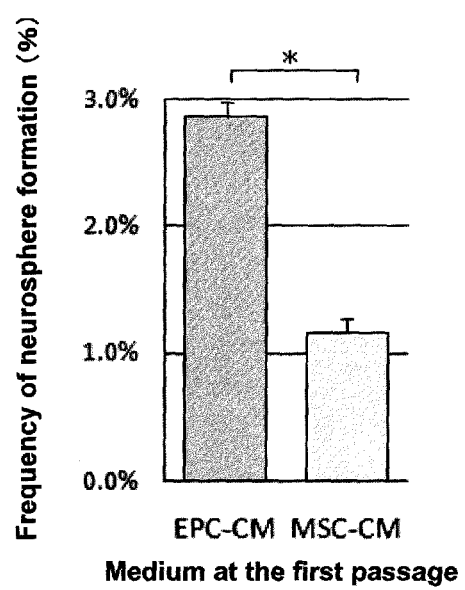
FIG. 5 is a graph showing a frequency of neurosphere formation when EPC-CM or MSC-CM was used as medium at the first passage of neural stem cells in one embodiment of the present invention.

In addition, as shown in FIG. 5, the frequency of tertiary neurosphere formation was significantly high in the group in which the cells were cultured with EPC-CM at the first passage, compared to the group in which the cells were cultured with MSC-CM at the first passage (t-test).

These results indicate that culture of the neural stem cells with EPC-CM promotes the self-renewal of these cells. It can be easily understood that the self-renewal is promoted by an effective substance other than the added growth factor, and that the effective substance is not contained in MSC-CM but is contained only in EPC-CM.

Example 3

This Example shows that a substance contained in EPC-CM which promotes the self-renewal of the neural stem cells is not any of the known growth factors.

ELISA was used to determine the amount of the growth factors (bFGF, EGF, VEGF, and BDNF) contained in EPC-CM and MSC-CM obtained in the aforementioned Examples 1 and 2, respectively. For this measurement, Quantikine FGF basic DFB50, Quantikine EGF MEG00, Quantikine VEGF MMV00, and Quantikine BDNF DBD00 ELISA kits (R & D) were used according to a manufacturer's instruction.

Figure 6:
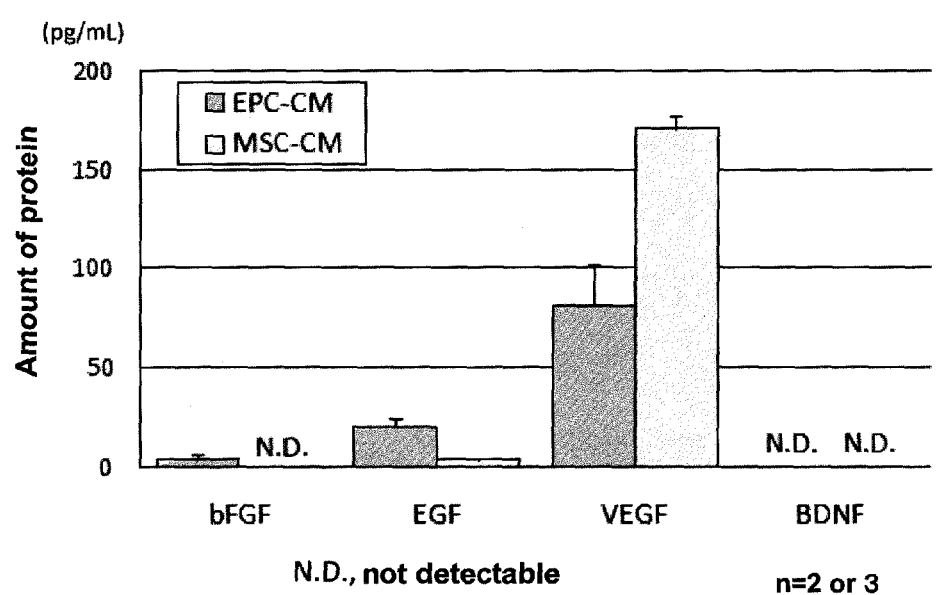
FIG. 6 is a graph showing an amount of growth factors contained in EPC-CM and MSC-CM in one embodiment of the present invention.

As shown in FIG. 6, growth factors other than BDNF are contained in EPC-CM and MSC-CM. In Examples 1 and 2, bFGF and EGF are contained more in EPC-CM having an effect of promoting the self-renewal of the neural stem cells.

Taking this into consideration, antibodies (Anti-basic FGF (#05-117, Upstate) and Anti-EGF (#06-102, Upstate)) against these growth factors were added to EPC-CM at a final concentration of 10 µg/ml and 20 µg/ml, respectively, to neutralize the factors, and the neurosphere assay described in Example 2 was performed. As a control group, MHM supplemented with 20 ng/ml of bFGF and 20 ng/ml of EGF (both are final concentration).

Figure 7:
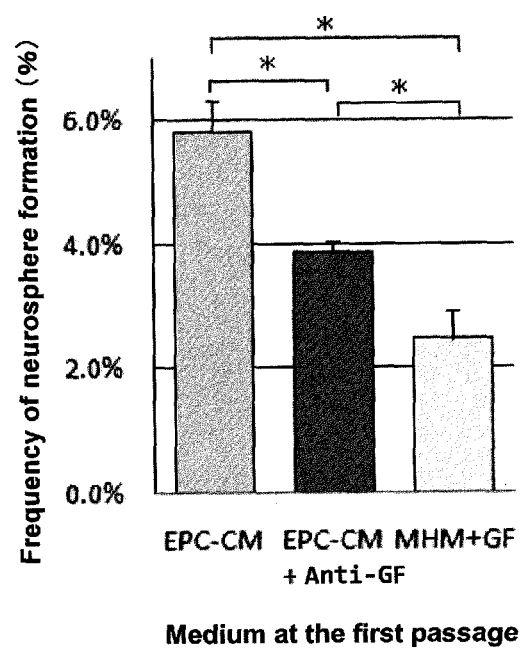
FIG. 7 is a graph showing a frequency of neurosphere formation in a EPC-CM group to which no antibody is added, a group in which growth factors contained in EPC-CM were neutralized with antibodies (EPC-CM+anti-GF group), and a group of MHM supplemented with growth factors (MHM+GF group) in one embodiment of the present invention.

As shown in FIG. 7, the frequency of tertiary neurosphere formation at the second passage in a group of EPC-CM containing antibodies (EPC-CM+anti-GF) was lower compared with a group of EPC-CM containing no antibody but was significantly higher compared with a group of MHM containing growth factors (MHM+GF) (t-test).

These results show that EPC-CM contains one or more substances that promote the self-renewal of the neural stem cells other than the known growth factors.

Example 4

In this Example, ECF-L is isolated, which is a protein contained in EPC-CM and promotes the self-renewal of neural stem cells.
==Fluorescent Two-Dimensional Difference Gel Electrophoresis==

Fluorescent two-dimensional difference gel electrophoresis (entrusted to Chemicals Assessment and Research Center, Chemicals Evaluation and Research Institute, Examination No. 937-07-P-1022) was used to search for substances that are contained in EPC-CM but are not contained in MSC-CM. A specific method of this experiment is described below.
(Reagents Used in this Example and their Suppliers)

Urea, dithiothreitol (DTT), Pharmalyte, glycerol, sodium dodecyl sulfate (SDS), trimethylolaminomethane hydrochloride (Tris), and Cy-Dye were purchased from GE Healthcare Biosciences, Inc., 3-[(3-cholamidopropyl)dimethylammonio]-1-propanesulfonate (CHAPS) and iodoacetamide were purchased from DOJINDO LABORATORIES, lysine was purchased from Sigma-Aldrich, acetic acid and formic acid (super special grade) were purchased from Wako Pure Chemical Industries, Ltd., methanol (HPLC grade) was purchased from Wako Pure Chemical Industries, Ltd., trypsin was purchased from Promega, multiple affinity removal spin cartridge, Ms-3 (0.45 ml pack) was purchased from Agilent Technologies, Inc., and Sypro Ruby was purchased from Molecular Probes.

(Pretreatment of Samples and Labeling Reaction)

Albumin, IgG, and transferrin in samples (EPC-CM and MSC-CM) were removed using a multiple affinity removal spin cartridge according to a protocol provided by Agilent. To the protein solution after the removal of the aforementioned proteins, a double volume of cold acetone was added, and the mixture was kept in a deep freezer (−80° C.) for 1 hour. The precipitated protein was centrifuged at 20,000×g for 20 minutes. The precipitate was dissolved in a lysis buffer (LB) with protease inhibitor (4% (w/v) CHAPS, 2 M thiourea, 8 M urea, 10 mM Tris-HCl, pH 8.8) and the solution was used as a sample for analysis. The concentration of protein in the samples was measured using the Bradford protein assay after re-dissolving the concentrated samples in LB. A pooled sample was prepared by mixing an equal weight of the treated EPC-CM and MSC-CM.

To the samples, 200 pmol of Cy-Dye (DMF solution, 1 μl) per 100 μg of the protein was added, which was left stand on ice for 30 minutes. After the reaction, an excess amount of lysine solution (10 mM solution, 1 μl) was added and kept for 10 minutes to stop the reaction. Finally, an equal amount of 2× sample buffer (8 M urea, 4% (w/v) CHAPS, 20 mg/ml DTT, 2% (v/v) Pharmalyte) was added and kept on ice for additional 10 minutes.

The pooled sample, EPC-CM, and MSC-CM were labeled with Cy2, Cy3, and Cy5, respectively. The labeling efficiency was examined by average intensity of fluorescence in each lane of the image of the SDS-polyacrylamide gel.

(Two-Dimensional Electrophoresis)

Two-dimensional electrophoresis was performed on three gels according to the following conditions (triplicate). Samples of 200 μg each were separated.

For the 1-D electrophoresis, Multiphore II (GE Healthcare Biosciences, Inc.) and IPG (Immobilized pH Gradient) Strips (24 cm, pI3-10, GE Healthcare Biosciences, Inc.) were used. The samples were applied using a cup loading strip holder. Isoelectric focusing was performed for 40 kVh in total. After this electrophoresis, the gel strips were equilibrated for 10 minutes each using solutions A and B obtained by adding 0.25% (w/v) DTT and 4.5% (w/v) iodoacetamide, respectively, to equilibration buffers (50 mM Tris, pH 8.8, 6 M urea, 30% glycerol, 2% SDS).

After completion of the equilibration, the second electrophoresis was performed using Ettan DALT II System (GE Healthcare Biosciences, Inc.) and 12% homogeneous gel with a two-dimensional SDS-polyacrylamide gel electrophoresis. The electrophoresis was performed at 3 W (at 15° C.) of constant power until dye front was completely eluted (for about 15 hours).

The images of the gel after electrophoresis were captured immediately with Typhoon (Amersham Biosciences Corp.) (Cy2: excitation at 480 nm, emission at 530 nm; Cy3: excitation at 540 nm, emission at 590 nm; Cy5: excitation at 625 nm, emission at 680 nm). The captured gel images were converted into TIFF format. Thereafter, Decyder DIA software (Amersham Biosciences Corp.) was used to detect protein spots on the captured images, filter out noise, and compare spot volumes of Cy dyes between individual spots on each gel for quantitative analysis. In addition, Decyder BVA software (AmershamBiosciences Corp.) was used for spot matching between gels and statistical analysis.

Figure 8:
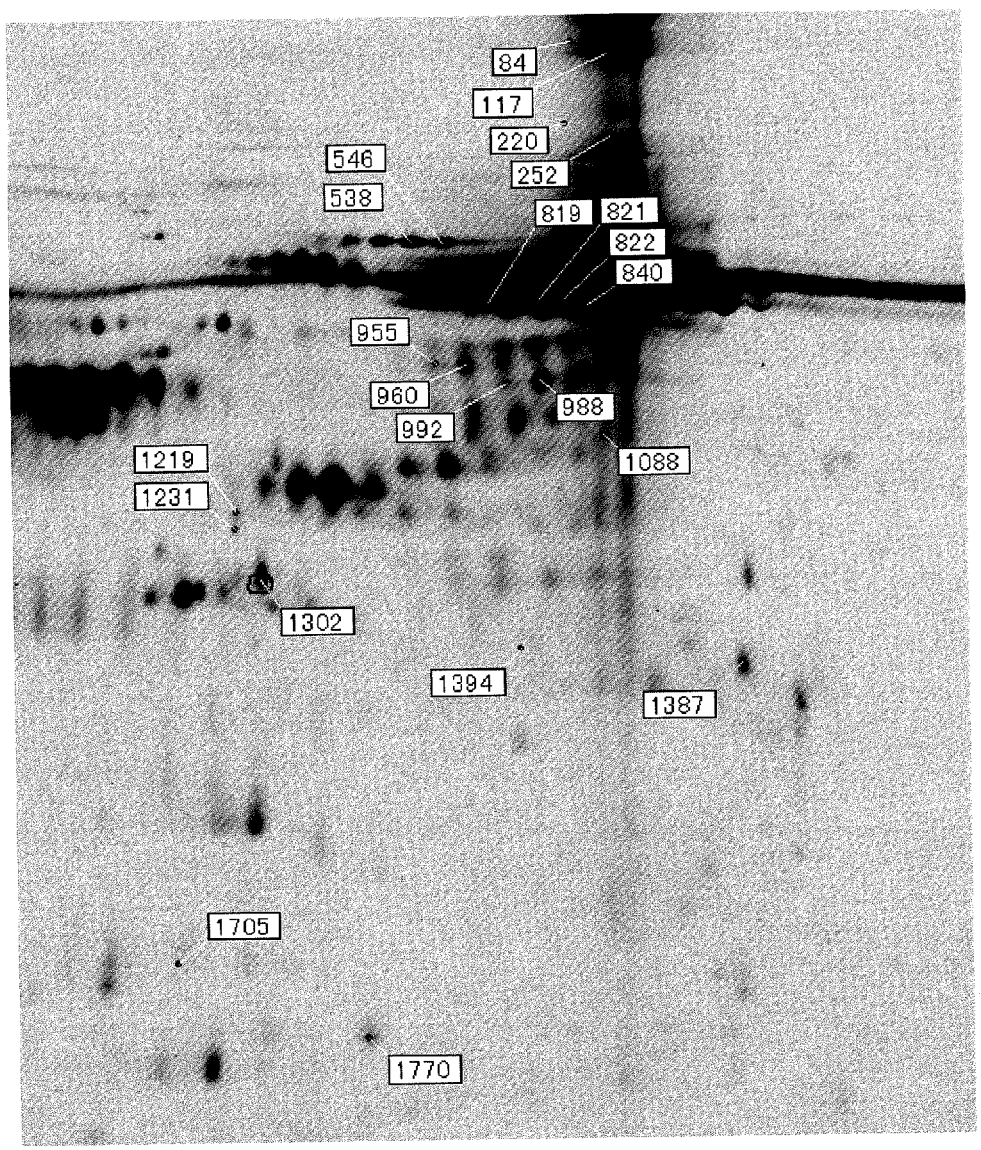
FIG. 8 is a photograph of a gel showing spots of proteins separated in two-dimensional electrophoresis of EPC-CM and MSC-CM in one embodiment of the present invention. The spots indicated by numbers in the figure are only those having MSC-CM/EPC-CM of smaller than ¼ ($p<0.01$)

FIG. 8 shows an image of the gel for two-dimensional electrophoresis. This figure includes only the spots for which the ratio of fluorescent intensities (MSC-CM/EPC-CM ratio) is smaller than ¼ (p<0.01). The ratio was calculated between fluorescent intensities of MSC-CM and EPC-CM captured in the manner described above and was represented as standardized log abundance. For the spots shown in the figure, average MSC-CM/EPC-CM values from three gel images and p values in study are given in Table 1.

TABLE 1

Spot Data for MSC-CM/EPC-CM < ¼ (p < 0.01)

| Spots | Average MSC-CM/EPC-CM value* | t-study (p value) |
|---|---|---|
| 1302 | −22.3 | 0.0005 |
| 822 | −20.37 | 0.0022 |
| 840 | −11.91 | 0.00091 |
| 84 | −9.56 | 0.0068 |
| 252 | −9.13 | 0.0071 |
| 821 | −8.69 | 0.001 |
| 988 | −7.05 | 0.0021 |
| 117 | −6.66 | 0.0025 |
| 1219 | −6.55 | 0.0051 |
| 960 | −6.47 | 0.0013 |
| 1231 | −6.35 | 0.005 |
| 992 | −5.96 | 0.0027 |
| 538 | −5.87 | 0.0017 |
| 546 | −5.23 | 0.0026 |
| 411 | −4.94 | 0.0095 |
| 1387 | −4.8 | 0.0047 |
| 1705 | −4.68 | 0.0029 |
| 819 | −4.39 | 0.0094 |
| 220 | −4.25 | 0.0048 |
| 244 | −4.24 | 0.0065 |
| 1770 | −4.17 | 0.003 |
| 1394 | −4.08 | 0.0084 |
| 955 | −4.06 | 0.0031 |
| 1088 | −4.05 | 0.0056 |

*For the MSC-CM/EPC-CM values in the table, an x-fold decrease is represented by −x, according to the Decyder BVA software.

==Identification of Protein in Spots by Mass Spectrometry==

With the aforementioned two-dimensional difference gel electrophoresis, samples containing 600 μg of protein were migrated under the same conditions. After the electrophoresis, the gel was immersed in fixative solution (10% methanol and 7% acetic acid) at room temperature for 30 minutes to fix the protein. After the fixation, the gel was immersed in 200 ml of Sypro Ruby stain (Molecular Probe) at room temperature for 3 hours. After completion of the staining, the gel was allowed to wash with a washing solution (10% methanol and 7% acetic acid) to remove excess stain.

The gel was scanned using MasterImager (Amersham Biosciences Corp.) to obtain images at an excitation wavelength (480 nm) and an emission wavelength (620 nm) of Sypro Ruby. After the staining, spots were matched in the gels for the analysis using the Decyder BVA software (Amersham Biosciences Corp.), and the spot 1302 in FIG. 8 and the Table 1 was excised using a spot picker (Ettan Spot Picker, Amersham Biosciences Corp.). The gel plug thus obtained was digested with 0.1 μg of trypsin (Promega) for each gel (30° C., overnight) and then analyzed using nano LC-ESI-MS (cap-LC (Waters), Q-T of micro (Micromass)). Analytical conditions for LC and MS are given below.

LC Conditions:
  Column: PepMap100 (75 μm ID×15 cm, 3 μm, 100 Å, S/N 31817)
  Column Temperature: room temperature
  Mobile Phase:
  [Solution A] 95/5 water/acetonitrile, 0.1% formic acid
  [Solution B] 5/95 water/acetonitrile, 0.1% formic acid
  Flow Rate: 2.5 μL/min.
  Gradient Condition Table 2

TABLE 2

| Time (min.) | Mobile Phase Composition (B %) |
|---|---|
| 3 | 5 |
| 35 | 40 |
| 36 | 80 |
| 41 | 80 |

MS Condition:
  MS measurement was performed in survey scan mode of Masslynx software (Micromass).
  Capillary Voltage: 3300 V
  Cone Voltage: 45 V
  Collision-induced Dissociation (CID) gas: argon
  Collision Energy: 25-35 eV
(Database Searches)

The data obtained from the MS/MS analysis was subjected to deconvolution using MassLynx (Micromass). A resulting peak list file (*.pkl) was used to query NCBInr (20070727: 5325920 sequences; 1842455067 residues) and Swiss-Prot (50.8: 234112 sequences; 85963701 residues) databases using the Mascot program (Matrix Science). The following modifications were set for the search: carbamidomethylation and methionine oxidation.

Tables 3 and 4 show results of Swiss-Prot search and NCBInr search, respectively. Seven peptides were found in these searches, and a corresponding protein was identified according to their amino acid sequences. The total score in the following Tables 3 and 4 was calculated based on the statistical probability. The score is reported as $-10 \log_{10}(P)$, where P is the probability that the identification of different proteins is a random event. A higher score indicates higher reliability.

TABLE 3

Result of Swiss-Prot Search (animal species: mouse)

| Spot | Protein Name | Accession No. | MW | pI | Score |
|---|---|---|---|---|---|
| 1302 | Chitinase 3-like protein 3 precursor (Secretory protein Ym1) (Eosinophil chemotactic cytokine) (ECF-L). | O35744 | 44772 | 5.42 | 370 |

TABLE 4

Result of NCBInr Search (animal species: mouse)

| Spot | Protein Name | gi No. | MW | pI | Score |
|---|---|---|---|---|---|
| 1302 | chitinase 3-like 3 [Mus musculus] | gi|6753416 | 44772 | 5.42 | 370 |

The above results indicate that the protein contained specifically in EPC-CM is ECF-L having a molecular weight of about 45 kDa.

Example 5

This Example shows that the ECF-L identified in Example 4 is a substance that promotes the self-renewal of the neural stem cells.

==Preparation of ECF-L Recombinant Protein==

E. coli DH10B TonA (30298306, ImaGenes) with pDNR-LIB vector into which cDNA encoding mouse Chitanase 3-like 3 (ECF-L) had been inserted was seeded in chloramphenicol (diluted in 100% ethanol to 30 mg/ml) selective LB medium and cultured at 37° C. On the following day, colonies were picked up and cultured with shaking overnight in chloramphenicol selective LB liquid medium, and then the plasmid was recovered using QIAprep Spin Miniprep Kit (Qiagen).

A reaction mixture (distilled water, 7.5 μl; 10×Cre Reaction Buffer (Clontech), 2 μl; 10×BSA, 2 μl; 200 ng Donor Vector, 7.0 μl; 200 ng Acceptor Vector, 0.5 μl; Cre Recominase (Clontech), 1 μl) was prepared in order to introduce the plasmid obtained into pLP-CMV-Myc Acceptor Vector (Catalog No. 631603, Clontech). This reaction mixture was incubated at room temperature for 15 minutes and then heated to 70° C. for 5 minutes to stop the reaction. One μl of this reaction mixture was mixed with DH5α competent cells, which was then incubated on ice for 15 minutes, heat-shocked at 42° C. for 30 seconds, and incubated on ice for additional 2 minutes for transformation. The DHα competent cells were seeded in chloramphenicol selective LB plates and cultured overnight. After the culture, larger colonies were picked up from the colonies obtained, and recombination of the plasmid was confirmed by colony PCR using the following primers.

```
CMV-F: GCTCACCGTCTTTCATTGCC    (SEQ ID No. 2)
CMV-R: TGTATCTTATCATGTCTGGATC  (SEQ ID No. 3)
```

Plasmid was recovered from the colonies where recombination was confirmed, using QIAprep Spin Miniprep Kit (Qiagen) and the sequence of the inserted DNA was confirmed. Prior to the transfection of cells for expressing protein, this desired plasmid was scaled up using QIAprep Spin Maciprep kit (Qiagen).

One day before transfection, 15 to 25×10$^5$ HEK293T cells were seeded per 10 cm of Poly-o-coated dish and incubated overnight at 37° C., 5% CO$_2$ so that the cells reached 50 to 80% confluent.

800 μl of medium (Opti-MEM) was put into a sterile culture tube to which 18 μl of GeneJuice Transfection Regent (Novagen) was added. This was suspended in a Vortex and incubated for 5 minutes. To this, 6 μg of plasmid DNA was added and mixed by pipetting. Thereafter, the mixture was incubated at room temperature for 5 to 15 minutes and added dropwise to the aforementioned HEK293T cells. The cells were incubated at 37° C., 5% CO$_2$ for 24 hours. Thereafter, a transfection mixture was removed and washed with MHM (without transferrin) three times, to which fresh MHM (with/without transferrin) was added in a volume of 1 ml per well.

==Detection of ECF-L Recombinant Protein by Western Blotting==

In order to confirm that ECF-L was secreted to the culture supernatant of the ECF-L gene-introduced HEK293T cells thus obtained, ECF-L contained in the culture supernatant of ECF-L gene-introduced HEK293T cells was detected by Western blotting. First, 1 ml of the culture supernatant of the ECF-L gene-introduced HEK293T cells was collected and concentrated through AmiconUltra-4 Centrifugal Filter Devices (10k NMWL, UFC801008, Millipore).

The concentrated culture supernatant was used as a sample, and 700 ng of protein was loaded per lane on an SDS-polyacrylamide gel for electrophoresis. The separated protein was blotted onto PVDF membrane.

After the blotting, the membrane was blocked with 5% skimmed milk (diluted in TEST (Tris-buffered saline with Tween 20)) at room temperature for 1 hour and incubated at room temperature for 1 hour or at 4° C. overnight with anti-mouse ECF-L rat monoclonal antibody (MAB2446, R&D systems, 1:250 dilution). Then, the membrane was washed with TEST for 5 to 10 minutes, and incubated at room temperature for 1 hour with horseradish peroxidase-conjugated anti-rat IgG goat antibody (Jackson ImmunoResearch, 1:5000 dilution). The membrane was washed with TEST again and then signals were detected using ECL Plus Western Blotting Detection System (RPN2132, GE).

Figure 9:
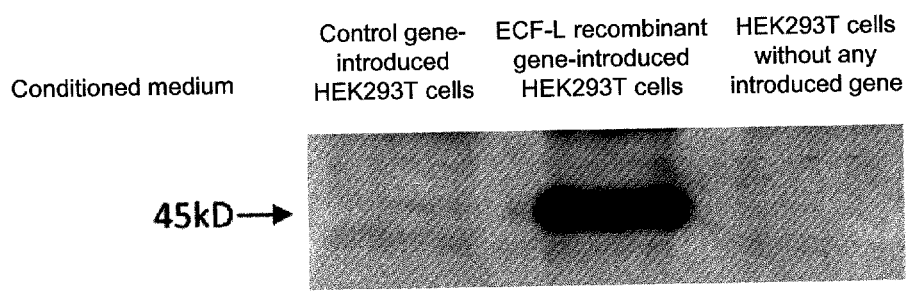
FIG. 9 is a figure showing a result of a Western blotting using a culture supernatant of HEK293T cells transfected to express ECF-L recombinant protein, control gene-introduced HEK293T cells, and HEK293T cells without exogenous gene in one embodiment of the present invention.

As shown in FIG. 9, a specific band was detected by anti-ECF-L antibody at or around 45 kDa. On the other hand, this band was not detected in a control gene group in which fluorescent protein, venus, was expressed using a similar manner and a non-recombinant group treated in a similar manner except that recombination of pLP-CMV-Myc Acceptor Vector with pDNR-LIB vector was not performed. These results indicate that the transfected HEK293T cells express recombinant ECF-L, and this ECF-L is secreted to the culture supernatant.

==Effect of ECF-L on Self-Renewal of Neural Stem Cells Derived from Fetal Mice==

It was verified that the recombinant ECF-L has an effect of promoting the self-renewal of the neural stem cells.

First, the "Assay of Neurospheres derived from Fetal Mice" described in Example 2 was performed (see, FIG. 3). In this case, at the first passage, cells were seeded in each well of the 6-well plate (9.6 cm$^2$) so that 10 to 15×10$^4$ cells exist per 3 ml of MHM containing ECF-L recombinant protein (RcECF-L), EPC-CM, ECF-L-depleted EPC-CM or MHM. The culture supernatant of ECF-L-expressing HEK293T cells obtained according to "Preparation of ECF-L Recombinant Protein" in this Example was used as the MHM containing ECF-L recombinant protein.

The ECF-L-depleted EPC-CM is a conditioned medium obtained by introducing the following siRNA into endothelial progenitor cells (EPCs) derived from bone marrow which was cultured for 14 days in Example 1 using x-tremeGENE siRNA Transfection Reagent (04 476 093 001, Roche) and then culturing for one week. The siRNA was created in Sigma-Aldrich Genosys siRNA service.

Figure 10:
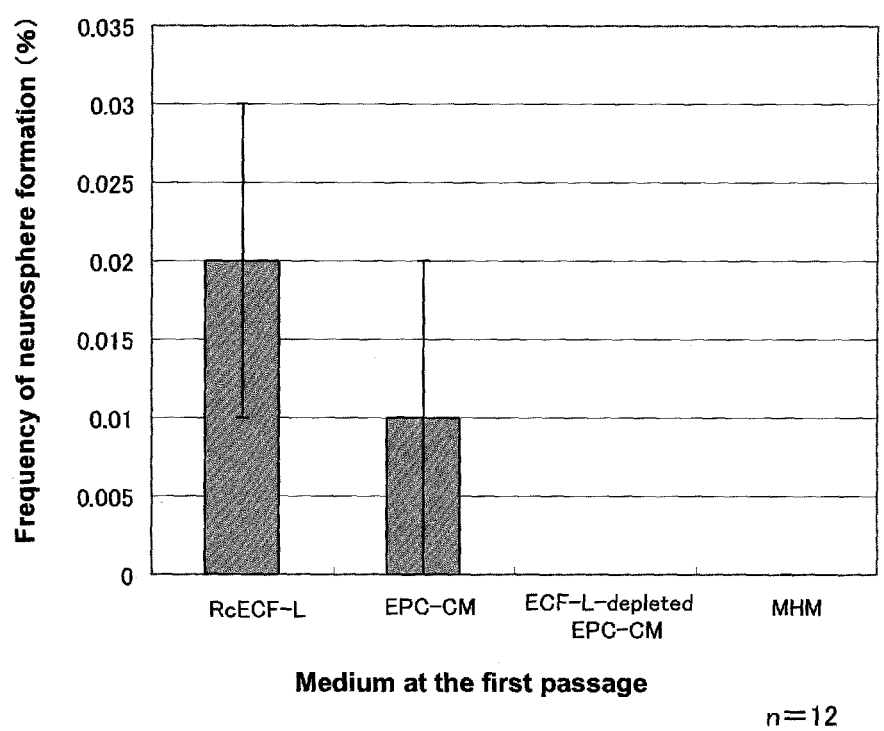
FIG. 10 is a graph showing a frequency of neurosphere formation when a neurosphere assay was performed for secondary neurospheres derived from fetal mice in a group cultured with either ECF-L recombinant protein-containing MHM group (RcECF-L), a group cultured with EPC-CM, a group cultured with ECF-L-depleted EPC-CM, and a group cultured with MHM, at the first passage, in one embodiment of the present invention.

(SEQ ID No. 4)
Sense strand: 5'-GAUCAAGUUCAACGGUUUUUC (SEQ ID No. 5)
Anti sense strand: 5'-AAAACCGUUGAACUUGAUCUU As shown in FIG. 10, the secondary neurospheres at the first passage were found only in the RcECF-L group and the EPC-CM group. On the other hand, no neurosphere was formed in the ECF-L-depleted EPC-CM group and the MHM group (n=12). The fact that neurospheres were formed in the EPC-CM group but not in the ECF-L-depleted EPC-CM, and neurospheres were formed in the RcECF-L group indicates that ECF-L are involved in the formation of the neurospheres.

Figure 11:
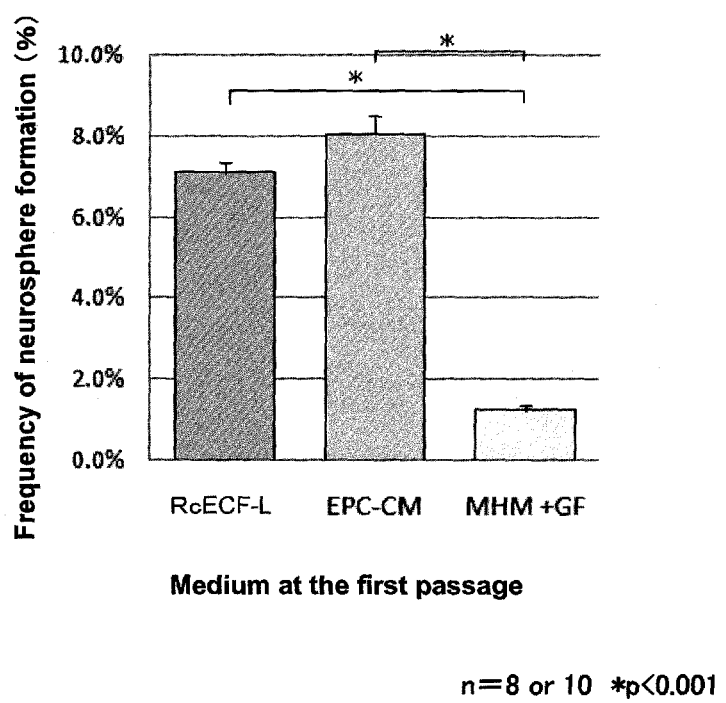
FIG. 11 is a graph showing a frequency of neurosphere formation in a group cultured with ECF-L recombinant protein-containing MHM group (RcECF-L), a group cultured with EPC-CM (EPC-CM), and a group cultured with MHM supplemented with growth factors (MHM+GF), at the first passage, when a neurosphere assay was performed for tertiary neurospheres derived from fetal mice in one embodiment of the present invention.

Furthermore, as shown in FIG. 11, the frequency of tertiary neurosphere formation in the RcECF-L group and the EPC-CM group was comparably high, and significantly higher than that in the group of MHM containing growth factors (MHM+GF) (t study).

==Effect of ECF-L on Self-Renewal of Neural Stem Cells Derived from Adult Mice==

In this example, it is verified that the recombinant ECF-L has an effect of promoting the self-renewal of the neural stem cells derived from the striatum of adult mice.

Adult mice (C57BL/6J, male, 8 to 10 weeks of age) were anesthetized with diethyl ether and sacrificed by decapitation or cervical spine dislocation. After these mice were wiped with alcohol, the scalp was incised from the neck to the orbit, and then the skull was incised. The skull was removed and the exposed brain tissue was kept in ice-cold PBSG. The striatum was isolated with ophthalmologic scissors and forceps and kept in a fresh ice-cold PBSG. This striatum was transferred to a centrifuge tube, and PBSG was replaced with a trypsin solution (40 mg of trypsin (T-1005, Sigma-Aldrich), 20 mg of hyaluronidase (H-6254, Sigma-Aldrich), and 6 mg of kynucreic acid (K-3375, Sigma-Aldrich) were dissolved in 30 ml of MHM and sterilized by filter sterilization). The tissue was disrupted by pipetting, digested at 37° C. for 15 minutes, and then disrupted again by pipetting. A trypsin inhibitor solution (8.4 mg of Trypsin inhibitor (ovomucoid) T-2011 (Sigma-Aldrich) was dissolved in 12 ml of MHM and sterilized by filter sterilization) was added to the disrupted tissue, which is centrifuged at 600 rpm for 5 minutes. The supernatant was discarded and 5 ml of trypsin inhibitor solution was added to the pellet, which was resuspended by pipetting. It was centrifuged at 600 rpm for 5 minutes. Then, the supernatant was discarded and the pellet was resuspended in 1 ml of MHM. The number of cells was counted by the method of counting living cells described above.

The cells thus obtained were seeded in a flask of 75 cm$^2$ containing MHM supplemented with 20 ng/ml of bFGF (Peprotech) and 20 ng/ml of EGF (both final concentration) to a density of 3,000 to 5,000 cells/ml and cultured at 37° C., 5% $CO_2$.

Most of the primary neurospheres were 100 μm or larger in diameter in about one week.

These primary neurospheres were subcultured as in the case of Example 2, and seeded in each well of a 6-well plate (9.6 cm$^2$) so that 10 to 15×10$^4$ cells were included per 3 ml of MHM containing ECF-L recombinant protein (RcECF-L) or MHM supplemented with growth factors and incubated at 37° C., 5% $CO_2$ for 7 days.

The secondary neurospheres thus obtained were centrifuged at 400 rpm for 5 minutes, after which the pellet was kept and the supernatant was filtered through a filter of 0.45 μm. To the pellet, 2 ml of filtered supernatant (filtered medium) was added. The secondary neurospheres were dissociated by pipetting to prepare cell suspension. This suspension was left stand for several minutes for precipitating the remaining neurospheres. The supernatant (1.5 ml) containing only the dispersed cells was transferred to a new centrifuge tube. Then, 1.5 ml of the filtered medium was added to the bottom layer containing the neurospheres, and the neurospheres were dissociated again by pipetting. This was left stand for 2 minutes and 1.5 ml of the supernatant thus obtained was mixed with the first supernatant collected previously. Then, 2 ml of the filtered medium was added thereto and the mixture was centrifuged at 800 rpm for 5 minutes. The supernatant was aspirated. 1 ml of 1:1 mixture of MHM supplemented with 20 ng/ml of bFGF and 20 ng/ml of EGF (both final concentration) and the culture supernatant of the primary culture of the neurospheres to the cell pellet and the cells were resuspended.

After the number of cells was counted by the method of counting living cells described above, the cells constituting the secondary neurospheres were adjusted to a density of 2 to 8×10$^6$ cells/ml using MHM-CM medium. To this cell suspension, 2 μg/ml of Propidium Iodide (Sigma-Aldrich) was added to label dead cells. From this suspension, living cells were separated by FACS and used for the following dispersed cell culture.

The living cells thus obtained were seeded in one well of a 96-well plate per each cell, and incubated at 37° C., 5% $CO_2$ for 10 days in 1:1 mixture of MHM supplemented with 1% penicillin G, streptomycin sulfate, 20 ng/ml of bFGF and 20 ng/ml of EGF (both final concentration) and the culture supernatant of the primary culture of the neurospheres. A percentage of the number of wells where neurospheres larger than 50 μm in diameter were formed with respect to the number of wells in which the cells were seeded was considered as a percentage of wells with neurosphere formation.

Figure 12:
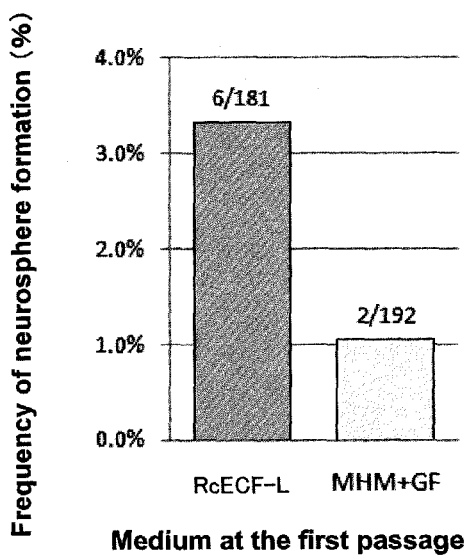
FIG. 12 is a graph showing a percentage of wells with neurosphere formation in a group cultured with ECF-L recombinant protein-containing MHM (RcECF-L) and a group cultured with MHM supplemented with growth factors (MHM-GF), at the first passage, when neural stem cells derived from adult mice were subjected to a dispersed cell culture in one embodiment of the present invention.

As shown in FIG. 12, the percentage of wells with neurosphere formation was higher in the group in which the cells were cultured at the first passage with MHM containing ECF-L recombinant protein (RcECF-L) compared to the group of MHM containing growth factors (MHM+GF). Since it is known that a certain percentage of neural stem cells give rise to neurospheres when a single cell was cultured under the aforementioned condition, the aforementioned percentage of wells with neurosphere formation relatively represents a percentage of neural stem cells in the aforementioned living cells.

The above results in this Example indicate that ECF-L has an effect of promoting the self-renewal of the neural stem cells obtained from fetal and adult mice. Accordingly, this ECF-L can be used in a promoting agent or a pharmaceutical composition for promoting the self-renewal of the neural stem cells. In addition, this pharmaceutical composition can be used to treat diseases caused by neuronal dysfunction.

Example 6

This Example shows that ECF-L is localized in the hippocampus and the subventricular zone where neural stem cells are present, and that ECF-L is physiologically affecting the neural stem cells.

==Creation of Mice with Transplanted GFP-Labeled Cells==

According to the aforementioned method of isolating cells derived from bone marrow, bone marrow cells were obtained from a CAG-EGFP mouse. These bone marrow cells were transplanted to recipient animals (C57BL/6J, male, 8 to 10 weeks of age) in a density of $2 \times 10^6$ cells per animal. The recipient animals were then exposed to radiation of 10.5 Gy and then were fed for 4 weeks or more.

Frozen coronal sections of mouse brain were created for untreated adult mice (C57BL/6J, male, 8 to 10 weeks of age) or mice with transplanted GFP-labeled cells derived from bone marrow as described above, using the aforementioned method of fixing mouse tissue and producing frozen sections. Next, each protein was labeled using the aforementioned immunohistochemical staining. For this purpose, PBS supplemented with 10% normal goat or donkey serum was used as a blocking buffer. For detection of ECF-L, rat anti-mouse ECF-L monoclonal antibody (MAB2446, R&D systems, 1:50 dilution) or goat anti-mouse ECF-L antibody (AF2446, R&D, 1:1000 dilution) was used as the primary antibody. For the detection of CD31, rat anti-mouse CD31 antibody (550274, BD Biosciences, 1:10 dilution) was used as the primary antibody. It is known that expression of CD31 is restricted to the endothelial cells. In addition, for the detection of GFAP (Glial fibrillary acidic protein), mouse monoclonal anti-GFAP antibody (G3893, Sigma-Aldrich, 1:100 dilution) was used as the primary antibody. With this mouse monoclonal anti-GFAP antibody, neural stem cells can be detected in the subventricular zone of the lateral ventricle. Furthermore, for the detection of aquaporin 4 (AQP4), rabbit anti-aquaporin 4 antibody (AB3594, Millipore, 1:200 dilution) was used as the primary antibody. It is known that expression of AQP4 in the brain is localized in astrocyte foot processes near blood vessels and that the local expression represents the existence of brain-blood barrier. As the secondary antibody, Alexa Fluor 488 goat anti-rat IgG antibody (A-11006, Molecular Probes, 1:500 dilution), Alexa Fluor 488 donkey anti-goat IgG antibody (A-11055, Molecular Probes, 1:500 dilution), Alexa Fluor 350 goat anti-mouse IgG antibody (A-11045, Molecular Probes, 1:500 dilution), Alexa Fluor 350 goat anti-rabbit IgG antibody (A-11046, Molecular Probes, 1:500 dilution), or Alexa Fluor 633 donkey anti-goat IgG antibody (A-21100, Molecular Probes, 1:500 dilution) was used when necessary. For CD31, signals were amplified using Tyramide Signal Amplification (Renaissance TSA fluorescence system, NEL702-705, Perkin Elmer). In addition, Hoechst 33258 (94403, Sigma-Aldrich) was used to counterstain nuclei, if necessary.

Figure 13:
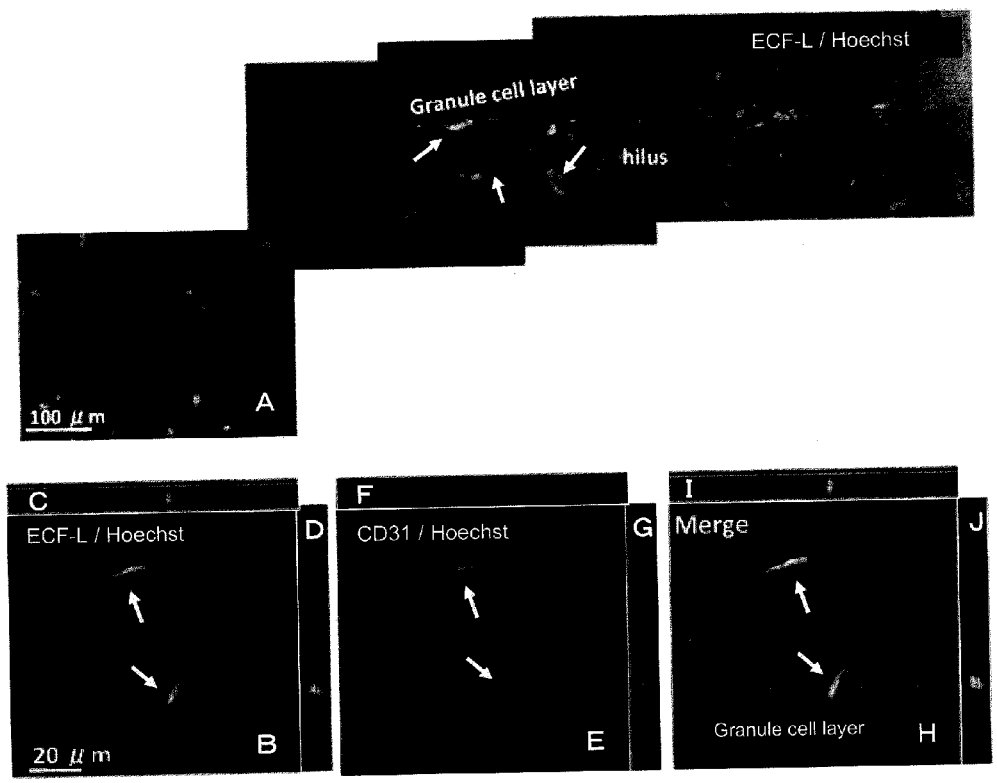
FIG. 13 shows micrographs showing localization of ECF-L (A, B, and C (section along XZ-axis), and D (section along YZ-axis)) and localization of CD31 (E, F (section along XZ-axis), and G (section along YZ-axis)), and co-localization of ECF-L and CD31 (H, I (section along XZ-axis), and J (section along YZ-axis)), in the hippocampus in one embodiment of the present invention.
Figure 14:
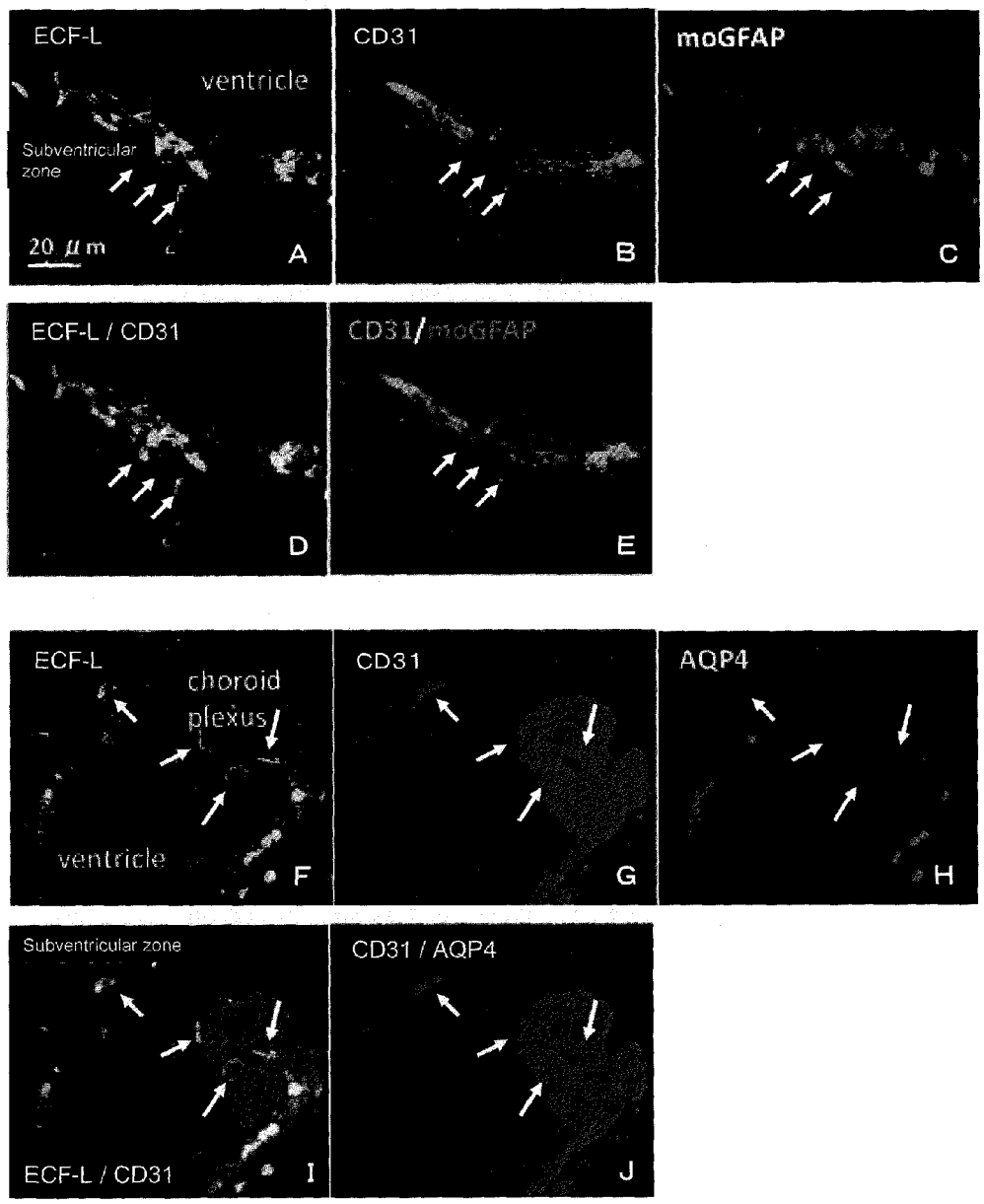
FIG. 14 shows micrographs showing localization of ECF-L (A and F), localization of CD31 (B and G), localization of GFAP (moGFAP) (C), localization of AQP4 (H), co-localization of ECF-L and CD31 (D and I), co-localization of CD31 and GFAP (E), and co-localization of CD31 and AQP4 (J), around the lateral ventricle in one embodiment of the present invention.
Figure 15:
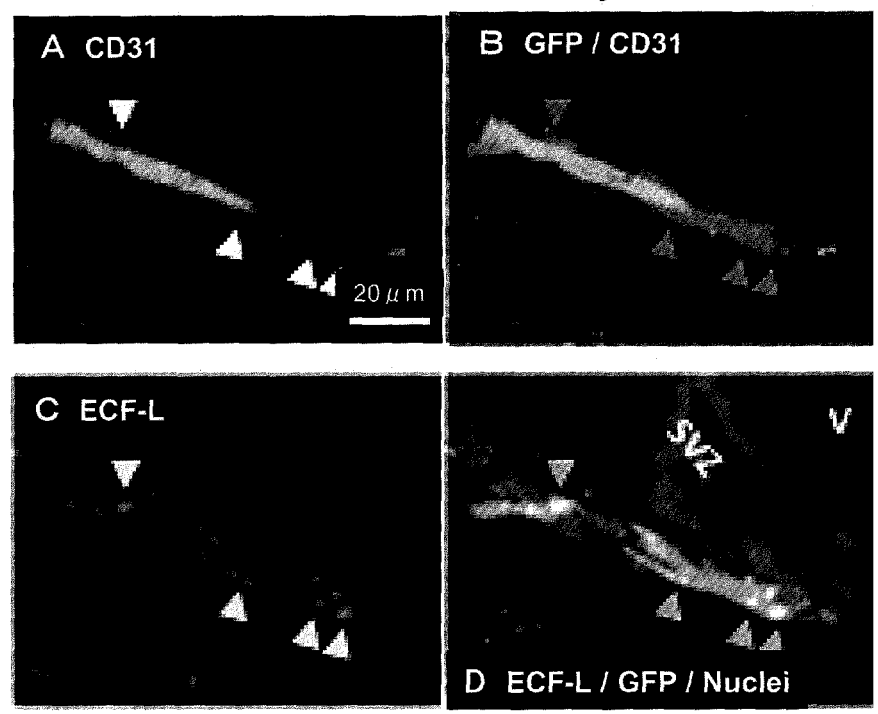
FIG. 15 shows micrographs showing localization of CD31 (A), localization of GFP (cells derived from the bone marrow) and localization of CD31 (B), localization of ECF-L (C), ECF-L, and GFP and localization of nuclei (D), in the lateral ventricle in one embodiment of the present invention.
Figure 16:
FIG. 16 shows micrographs showing localization of CD31 (A), localization of ECF-L (B, no signal), ECF-L, and GFP (no signal), and localization of nuclei (C), in the cerebral cortex in one embodiment of the present invention.

As shown in FIG. 13, ECF-L was found to be localized in the endothelial cells where CD31 is localized, in the hippocampus (A to J, arrows). In addition, as shown in FIG. 14, ECF-L was found to be co-localized in the endothelial cells where CD31 (B) is localized, in particular, at regions contacting the neural stem cells positive for GFAP (C, moGFAP in the figure), in the subventricular zone of the lateral ventricle (A to E). Furthermore, AQP4 (H) which is a marker of the brain-blood barrier was not found to be localized in the endothelial cells where CD31 (G) and ECF-L (F) are co-localized, in the subventricular zone of the lateral ventricle and the choroid plexus (F to J, arrows). Thus, it is suggested that ECF-L in the choroid plexus is expressed in the endothelial cells where no brain-blood barrier is present. In addition, as shown in FIG. 15, expression of ECF-L was detected in the GFP-labeled endothelial cells originating from bone marrow where CD31 is localized (A to D, arrow heads). The GFP-labeled endothelial cells originating from bone marrow are neovessels generated after the transplantation of the GFP-labeled bone marrow cells to the recipient, indicating that ECF-L is expressed in the neovessels. On the other hand, as shown in FIG. 16, in the cerebral cortex, neither the GFP label indicative of neovessels originating from the transplanted bone marrow nor the localization of ECF-L were found in the endothelial cells where cells originating from bone marrow and CD31 are localized (A to C).

Thus, ECF-L is specifically expressed in the endothelial cells of neovessels in the hippocampus and the subventricular zone. The hippocampus and the subventricular zone are regions where neural stem cells are mainly found, so that this expression pattern confirms that ECF-L affects the neural stem cells from the physiological viewpoint as well.

Example 7

This Example shows that neurospheres prepared by acting ECF-L in vitro differentiate into neurons at a high efficiency.

Primary neurospheres were prepared using striatum cells isolated from adult mice (n=8) according to the description of "Effect of ECF-L on self-renewal of neural stem cells derived from adult mice" in Example 5, and subcultured once. At the first passage, cells were seeded in each well of the 6-well plate (9.6 cm$^2$) so that 10 to $15 \times 10^4$ cells were included per 3 ml of MHM containing ECF-L recombinant protein (RcECF-L group), MHM containing ECF-L recombinant protein supplemented with growth factors (20 ng/ml of bFGF and 20 ng/ml of EGF) (RcECF-L+GF group), EPC-CM (EPC-CM group), MHM containing ECF-L-depleted EPC-CM supplemented with growth factors (ECF-L-depleted EPC-CM+GF group) or MHM containing growth factors (MHM+GF group), and incubated at 37° C., 5% $CO_2$ for 7 days. ECF-L-depleted EPC-CM was prepared according to the description in Example 5. In addition, for MHM containing ECF-L recombinant protein, the culture supernatant of ECF-L-expressing HEK293T cells obtained according to "Preparation of ECF-L recombinant protein" in Example 5 was used.

Next, for the secondary neurospheres obtained, the aggregates were disrupted and the number of cells was counted according to the description of "Effect of ECF-L on Self-renewal of Neural Stem Cells derived from Adult Mice" in Example 5. The cells were seeded in each well of a 96-well plate per one cell to form tertiary neurospheres.

The tertiary neurospheres were placed on a chamber slide (#5732-008, Iwaki) coated with poly-L-ornithine and fibronectin, seeded in MHM supplemented with 1% FBS to a density of $1\times10^4$ cells/ml, and incubated at 37° C., 5% $CO_2$ to differentiate them (FIG. 3). The medium was discarded after 4 days from the beginning of culture and the cells were fixed with 4% paraformaldehyde.

The fixed cells were labeled using the aforementioned immunohistochemical staining. For this purpose, PBS supplemented with 10% normal goat serum was used as a blocking buffer. For the detection of β-tubulin III, immunohistochemical staining was performed using mouse monoclonal anti-human-β-tubulin III antibody (T8660, Sigma-Aldrich, 1:1000 dilution) as the primary antibody and Alexa Fluor 555 goat anti-mouse IgG antibody (A-11031, Molecular Probes, 1:1000 dilution) as the secondary antibody. In addition, for the detection of O4, mouse anti-O4 monoclonal antibody (MAB345, Millipore, 1:1000 dilution) was used as the primary antibody and Alexa Fluor 488 goat anti-mouse IgM antibody (A-21042, Molecular Probes, 1:500 dilution) was used as the secondary antibody. For the detection of GFAP, rabbit anti-GFAP antibody (Z0334, Dako, 1:2000 dilution) was used as the primary antibody and Alexa Fluor 350 goat anti-rabbit IgG antibody (A-21068, Molecular Probes, 1:500 dilution) was used as the secondary antibody. It is known that β-tubulin III is localized in neonatal neurons, O4 is localized in oligodendrocytes and GFAP is localized in astrocytes.

For quantitative analysis, the numbers of β-tubulin III positive cells, O4 positive cells, and GFAP positive cells were counted in five fields under a microscope.

Figure 17:
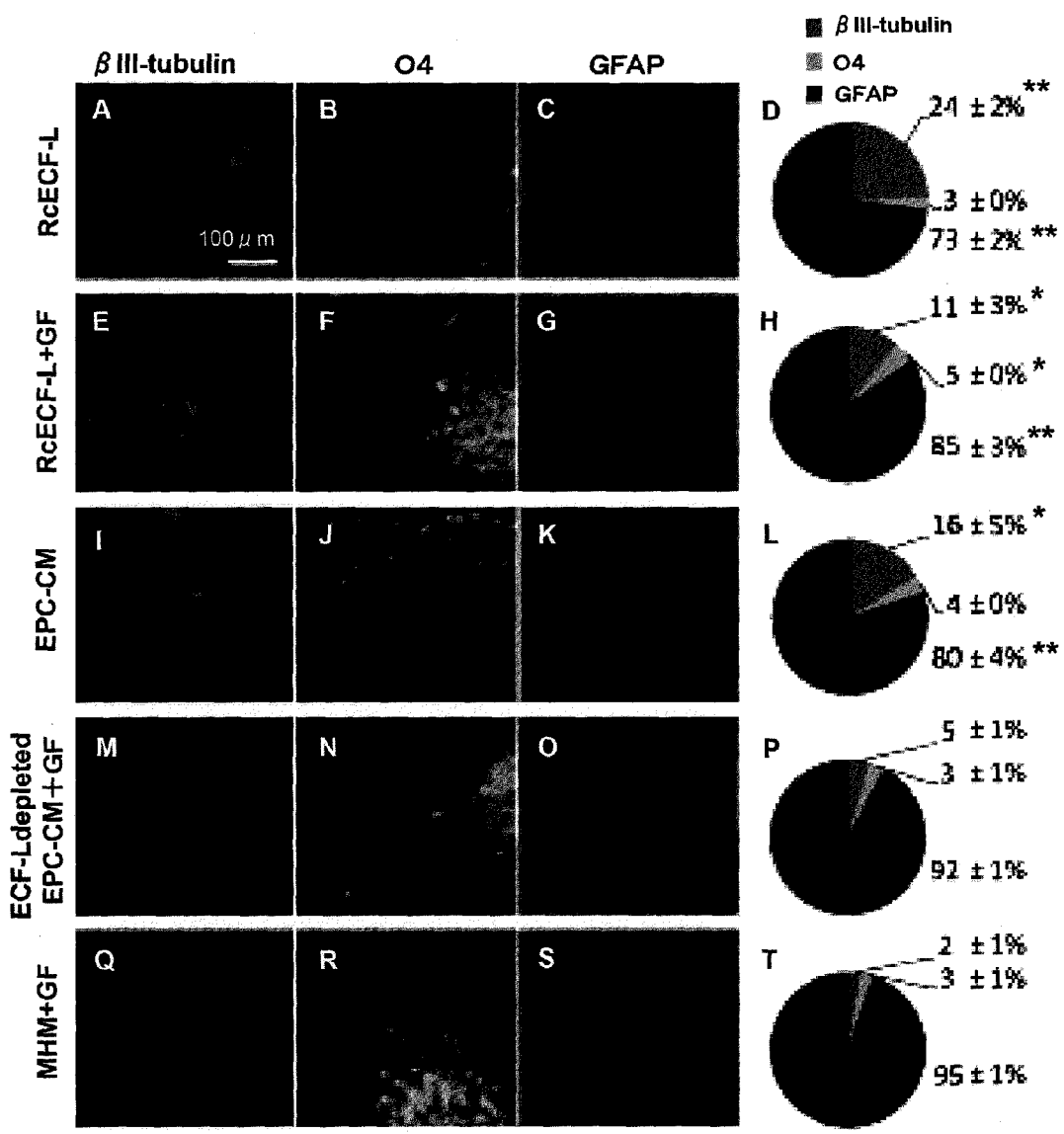
FIG. 17 shows micrographs showing labels with β-tubulin III (A, E, I, M, and Q), O4 (B, F, J, N, and R), and GFAP (C, G, K, O, and S) in cells differentiated from tertiary neurospheres and a graph showing a ratio of β-tubulin III positive cells, O4 positive cells, and GFAP positive cells (D, H, L, P, and T), when neurospheres were cultured at the first passage in ECF-L recombinant protein-containing MHM (RcECF-L group), ECF-L recombinant protein-containing MHM supplemented with a growth factor (RcECF-L+GF group), EPC-CM (EPC-CM group), MHM in which a growth factor was added to ECF-L-depleted EPC-CM (ECF-L-depleted EPC-CM+GF group) or MHM supplemented with growth factors (MHM+GF group) in one embodiment of the present invention.

As shown in FIG. 17, in the cells differentiated from the cultured tertiary neurospheres, β-tubulin III positive cells, O4 positive cells, and GFAP positive cells were differentiated through different pathways depending on the medium used at the first passage. The RcECF-L group (A to D), the RcECF-L+GF group (E to H), and the EPC-CM group (I to L) had a higher percentage of β-tubulin III positive cells and a lower percentage of GFAP positive cells, compared to the MHM+GF group (Q to T). On the other hand, the ECF-L-depleted EPC-CM+GF group are similar to the HMH+GF group in percentage of β-tubulin III positive cells and GFAP positive cells. No difference in percentage of O4 positive cells was found among the groups.

Thus, more cells that are differentiated from the tertiary neurospheres can be differentiated into neurons by acting ECF-L or EPC-CM on the cells during the culture at the first passage. In culture conditions, neurospheres tend to differentiate into glial precursors rather than into neurons with time due to asymmetric division. This result shows that ECF-L or EPC-CM suppresses the asymmetric division as well as the accompanying differentiation into glial precursors and promotes the self-renewal, which contributes to increasing the percentage of neurons after differentiation.

Example 8

This Example shows that ECF-L has an effect of promoting the self-renewal of the neural stem cells even in vivo, and that the neural stem cells obtained from the striatum of mice with the cerebral ventricle infused with ECF-L are differentiated into neurons at a high efficiency.

First, according to the "Attachment of infusion assembly to brain of mice" in Example 1, an infusion assembly was placed to infuse ECF-L into the cerebral ventricle of mice. Mice were fed for 7 days while infusing, at a rate of 0.5 µl per hour, MHM supplemented with ECF-L recombinant protein that was prepared in Example 5 and concentrated about 45 times (n=5). Mice in the control group were infused with an equal volume of concentrated MHM in place of the concentrated ECF-L-containing MHM. To concentrate the MHM medium supplemented with ECF-L recombinant protein, it was filtered by centrifugation at 2380×g for 30 minutes using Amicon Ultra 15 centrifuge filter devices (10K NMWL, UFC9010, Millipore).

Subsequently, skin and the skull were incised symmetrically between the skull and the eyes of each head under a stereomicroscope. Then, the brain tissue was opened to expose the lateral ventricle. A gray striatum found in a lumen of the lateral ventricle was isolated with ophthalmologic scissors and forceps and placed in a new 10-cm dish containing ice-cold PBSG. The brain tissue isolated in the manner described above was transferred to a centrifuge tube containing 800 µl of MHM and dissociated by pipetting. The number of cells was counted by the method of counting living cells as described above.

The cells thus obtained were placed on a chamber slide (#5732-008, Iwaki) coated with poly-L-ornithine and fibronectin, seeded in MHM supplemented with 1% FBS to a density of $1\times10^4$ cells/ml, and incubated at 37° C., 5% $CO_2$. 1 µM of BrdU was added to this medium, to label newly proliferated cells. The medium was discarded after 4 days from the beginning of culture and the cells were fixed with 4% paraformaldehyde.

Next, the fixed cells were incubated with 1 N HCl at 37° C. for 30 minutes, and then labeled using the immunohistochemical staining. For this purpose, PBS supplemented with 10% normal goat serum was used as a blocking buffer. BrdU was detected using sheep anti-BrdU antibody (20-BS17, Fitzgerald, 1:500 dilution) as the primary antibody and Alexa Fluor 568 donkey anti-sheep IgG antibody (A-21099, Molecular Probes, 1:1000 dilution) as the secondary antibody. In addition, immunohistochemical staining was performed to examine the localization of β-tubulin III in the same sample using mouse monoclonal anti-human-β-tubulin III antibody (T8660, Sigma-Aldrich, 1:1000 dilution) as the primary antibody and Alexa Fluor 555 goat anti-mouse IgG antibody (A-11031, Molecular Probes, 1:1000 dilution) as the secondary antibody. It is known that β-tubulin III is a marker for young neurons.

For quantitative analysis, the numbers of BrdU positive cells and β-tubulin III positive cells were counted in five fields under a microscope.

Figure 18:
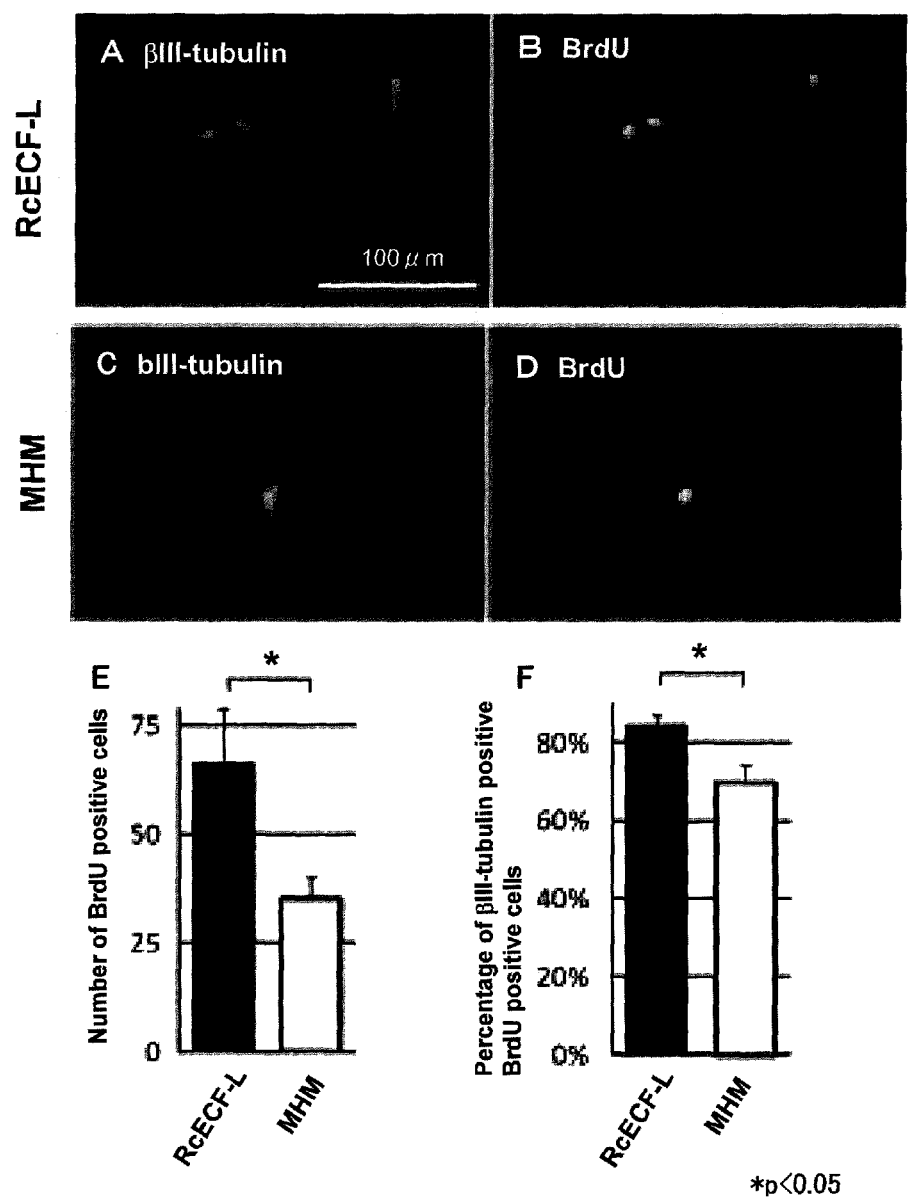
FIG. 18 shows micrographs showing β-tubulin III positive cells (A and C) and BrdU positive cells (B and D), in cells cultures and differentiated in BrdU-containing MHM (containing 1% FBS) from cells isolated from the striatum of an animal into which ECF-L (RcECF-L) or MHM was infused in vivo, a graph showing the number of BrdU positive cells (E), and a graph showing the number of double positive cells that are β-tubulin III positive and BrdU positive (neonatal neurons) (F) in one embodiment of the present invention.

As shown in FIG. 18, more BrdU positive cells were detected in the ECF-L infusion group (RcECF-L) compared to the control group (MHM) (B, D, E). Cells that are β-tubulin III positive (A, C) and BrdU positive (B, D) are young newborn neurons because β-tubulin III labels young neurons and BrdU labels newborn cells. A ratio of these young newborn neurons to total newborn cells (a ratio of double positive cells to all BrdU positive cells) was significantly higher in the ECF-L group compared to the control group (F).

Thus, ECF-L has an effect of increasing the number of the neural stem cells by suppressing asymmetric division and accompanying differentiation into glial progenitors, even in vivo and promoting the self-renewal of the neural stem cells.

Furthermore, a percentage of neural stem cells to be differentiated into neurons increases when they are affected by ECF-L.

INDUSTRIAL APPLICABILITY

The present invention can provides an agent for promoting the self-renewal of the neural stem cells and a method of using the same.

The invention claimed is:

1. A method of culturing neural stem cells, comprising: culturing the neural stem cells in a medium comprising an effective amount of a chitinase 3-like 3 protein to promote self-renewal of the neural stem cells in culture, wherein the chitinase 3-like 3 protein is a recombinant protein.

2. The method according to claim 1, wherein the chitinase 3-like 3 protein is Ym1.

* * * * *

SEQUENCE LISTING

```
<160> NUMBER OF SEQ ID NOS: 5

<210> SEQ ID NO 1
<211> LENGTH: 398
<212> TYPE: PRT
<213> ORGANISM: Mus musculus

<400> SEQUENCE: 1

Met Ala Lys Leu Ile Leu Val Thr Gly Leu Ala Ile Leu Leu Asn Val
1               5                   10                  15

Gln Leu Gly Ser Ser Tyr Gln Leu Met Cys Tyr Tyr Thr Ser Trp Ala
            20                  25                  30

Lys Asp Arg Pro Ile Glu Gly Ser Phe Lys Pro Gly Asn Ile Asp Pro
        35                  40                  45

Cys Leu Cys Thr His Leu Ile Tyr Ala Phe Ala Gly Met Gln Asn Asn
    50                  55                  60

Glu Ile Thr Tyr Thr His Glu Gln Asp Leu Arg Asp Tyr Glu Ala Leu
65                  70                  75                  80

Asn Gly Leu Lys Asp Lys Asn Thr Glu Leu Lys Thr Leu Leu Ala Ile
                85                  90                  95

Gly Gly Trp Lys Phe Gly Pro Ala Pro Phe Ser Ala Met Val Ser Thr
            100                 105                 110

Pro Gln Asn Arg Gln Ile Phe Ile Gln Ser Val Ile Arg Phe Leu Arg
        115                 120                 125

Gln Tyr Asn Phe Asp Gly Leu Asn Leu Asp Trp Gln Tyr Pro Gly Ser
    130                 135                 140

Arg Gly Ser Pro Pro Lys Asp Lys His Leu Phe Ser Val Leu Val Lys
145                 150                 155                 160

Glu Met Arg Lys Ala Phe Glu Glu Glu Ser Val Glu Lys Asp Ile Pro
                165                 170                 175

Arg Leu Leu Leu Thr Ser Thr Gly Ala Gly Ile Ile Asp Val Ile Lys
            180                 185                 190

Ser Gly Tyr Lys Ile Pro Glu Leu Ser Gln Ser Leu Asp Tyr Ile Gln
        195                 200                 205

Val Met Thr Tyr Asp Leu His Asp Pro Lys Asp Gly Tyr Thr Gly Glu
    210                 215                 220

Asn Ser Pro Leu Tyr Lys Ser Pro Tyr Asp Ile Gly Lys Ser Ala Asp
225                 230                 235                 240

Leu Asn Val Asp Ser Ile Ile Ser Tyr Trp Lys Asp His Gly Ala Ala
                245                 250                 255

Ser Glu Lys Leu Ile Val Gly Phe Pro Ala Tyr Gly His Thr Phe Ile
            260                 265                 270

Leu Ser Asp Pro Ser Lys Thr Gly Ile Gly Ala Pro Thr Ile Ser Thr
        275                 280                 285

Gly Pro Pro Gly Lys Tyr Thr Asp Glu Ser Gly Leu Leu Ala Tyr Tyr
    290                 295                 300
```

```
Glu Val Cys Thr Phe Leu Asn Glu Gly Ala Thr Glu Val Trp Asp Ala
305                 310                 315                 320

Pro Gln Glu Val Pro Tyr Ala Tyr Gln Gly Asn Glu Trp Val Gly Tyr
                325                 330                 335

Asp Asn Val Arg Ser Phe Lys Leu Lys Ala Gln Trp Leu Lys Asp Asn
            340                 345                 350

Asn Leu Gly Gly Ala Val Val Trp Pro Leu Asp Met Asp Asp Phe Ser
        355                 360                 365

Gly Ser Phe Cys His Gln Arg His Phe Pro Leu Thr Ser Thr Leu Lys
        370                 375                 380

Gly Asp Leu Asn Ile His Ser Ala Ser Cys Lys Gly Pro Tyr
385                 390                 395

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
gctcaccgtc tttcattgcc                                              20

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
tgtatcttat catgtctgga tc                                           22

<210> SEQ ID NO 4
<211> LENGTH: 21
<212> TYPE: DNA
<213> ORGANISM: Artificial Sequence
<220> FEATURE:
<223> OTHER INFORMATION: siRNA

<400> SEQUENCE: 4
gaucaaguuc aacgguuuuu c                                            21

<210> SEQ ID NO 5
<211> LENGTH: 21
<212> TYPE: DNA
<213> ORGANISM: Artificial Sequence
<220> FEATURE:
<223> OTHER INFORMATION: siRNA

<400> SEQUENCE: 5
aaaaccguug aacuugaucu u                                            21
```